US008668918B2

(12) United States Patent
Hong et al.

(10) Patent No.: US 8,668,918 B2
(45) Date of Patent: Mar. 11, 2014

(54) BISUREA GELLING AGENTS AND COMPOSITIONS

(75) Inventors: Xiaoyong Michael Hong, Greer, SC (US); Dominick J. Valenti, Moore, SC (US); Philip G. Harris, Spartanburg, SC (US); Laurent D. Kieken, Greenville, SC (US)

(73) Assignee: Milliken & Company, Spartanburg, SC (US)

(*) Notice: Subject to any disclaimer, the term of this patent is extended or adjusted under 35 U.S.C. 154(b) by 0 days.

(21) Appl. No.: 13/595,080

(22) Filed: Aug. 27, 2012

(65) Prior Publication Data
US 2013/0224139 A1   Aug. 29, 2013

Related U.S. Application Data

(60) Provisional application No. 61/530,045, filed on Sep. 1, 2011.

(51) Int. Cl.
*A61K 8/02* (2006.01)
(52) U.S. Cl.
USPC ........................................................ 424/401
(58) Field of Classification Search
None
See application file for complete search history.

(56) References Cited

U.S. PATENT DOCUMENTS

| | | |
|---|---|---|
| 2,710,839 A | 6/1955 | Swakon et al. |
| 2,967,178 A | 1/1961 | Kerr et al. |
| 3,242,210 A | 3/1966 | Dreher et al, |
| 3,679,068 A | 7/1972 | Peterson |
| 3,887,692 A | 6/1975 | Gilman |
| 3,893,956 A | 7/1975 | Brandt |
| 3,904,741 A | 9/1975 | Jones et al. |
| 4,049,792 A | 9/1977 | Elsnau |
| 4,104,177 A | 8/1978 | Caruso |
| 4,111,822 A | 9/1978 | Caruso |
| 4,120,948 A | 10/1978 | Shelton |
| 4,129,512 A | 12/1978 | Kisselow et al. |
| 4,160,754 A | 7/1979 | Schapel et al. |
| 4,261,845 A | 4/1981 | Cuscurida |
| 4,359,456 A | 11/1982 | Gosling et al. |
| 4,521,330 A | 6/1985 | Olstowski et al. |
| 4,529,530 A | 7/1985 | Shimizu et al. |
| 4,594,373 A | 6/1986 | Kohli |
| 4,661,276 A | 4/1987 | Stemke |
| 4,722,835 A | 2/1988 | Schamper et al. |
| 4,725,430 A | 2/1988 | Schamper et al. |
| 4,781,917 A | 11/1988 | Luebbe et al. |
| 4,816,261 A | 3/1989 | Luebbe et al. |
| 5,019,375 A | 5/1991 | Tanner et al. |
| 5,039,458 A | 8/1991 | Braatz et al. |
| 5,069,897 A | 12/1991 | Orr |
| 5,096,978 A | 3/1992 | Coran |
| 5,166,234 A | 11/1992 | Kawaguchi |
| 5,200,174 A | 4/1993 | Gardlik et al. |
| 5,346,694 A | 9/1994 | Juneja |
| 5,362,375 A | 11/1994 | Kubo et al. |
| 5,376,363 A | 12/1994 | Benfatto et al. |
| 5,405,605 A | 4/1995 | Shin |
| 5,429,816 A | 7/1995 | Hofrichter et al. |
| 5,451,396 A | 9/1995 | Villars |
| 5,462,684 A | 10/1995 | Naka et al. |
| 5,490,979 A | 2/1996 | Kasat et al. |
| 5,505,937 A | 4/1996 | Castrogiovanni et al. |
| 5,512,188 A | 4/1996 | Kinoshita et al. |
| 5,554,586 A | 9/1996 | Pratt |
| 5,609,855 A | 3/1997 | Oh et al. |
| 5,919,441 A | 7/1999 | Mendolia et al. |
| 6,066,313 A | 5/2000 | Anton et al. |
| 6,214,778 B1 | 4/2001 | Todd |
| 6,265,359 B1 | 7/2001 | Parthiban et al. |
| 6,355,602 B1 | 3/2002 | Okaniwa et al. |
| 6,517,821 B1 | 2/2003 | Rollat et al. |
| 6,908,621 B2 | 6/2005 | Jose et al. |
| 7,332,529 B2 * | 2/2008 | Carr ................................ 516/20 |
| 8,003,086 B2 | 8/2011 | Chodorowski-Kimmes |
| 2001/0051171 A1 | 12/2001 | Mondet |
| 2002/0159961 A1 | 10/2002 | Yamato et al. |
| 2002/0183213 A1 | 12/2002 | Komiya et al. |
| 2003/0021815 A9 | 1/2003 | Mondet et al. |

(Continued)

FOREIGN PATENT DOCUMENTS

| | | |
|---|---|---|
| CA | 1 164 347 | 3/1984 |
| CA | 2 064 179 | 11/1992 |

(Continued)

OTHER PUBLICATIONS

International Search Report. International application No. PCT/US2012/052993, International filed Aug. 30, 2012.

The Design of Organic Gelators: Solution and Solid State Properties of a Family of Bis-Ureas. Tetrahedron Letters 39 (1998) 7447-7450. Pergamon. Andrew J. Carr, Rosa Melendez, Steven J. Geib, Andrew D. Hamilton.

(Continued)

*Primary Examiner* — Susan Tran
(74) *Attorney, Agent, or Firm* — Brenda D. Wentz

(57) ABSTRACT

Bisurea gelling agents that impart a number of unexpected benefits within various gelled formulations and exhibit great versatility in terms of gelling capabilities for many types of solvents are provided. Such gelling agents should include pendant groups, such as sterically hindering alkyl groups attached to polyoxyalkylenated moieties that allow the gelling agent to be compatible with the target liquid system at elevated temperatures, while controlling and/or limiting the network formation and strength during the cooling cycle. Alternatively, novel gelling agents having two urea groups but that are asymmetrical in configuration have been produced in order to provide the same control in temperature, compatibility, and efficiency. Final gelled formulations, such as antiperspirant sticks and other like consumer items, are provided as well within this invention.

29 Claims, No Drawings

(56) References Cited

U.S. PATENT DOCUMENTS

| | | |
|---|---|---|
| 2003/0031638 A1 | 2/2003 | Joshi et al. |
| 2003/0064959 A1 | 4/2003 | Sawada et al. |
| 2003/0091520 A1 | 5/2003 | Livoreil et al. |
| 2007/0098658 A1 | 5/2007 | Chodorowski-Kimmes et al. |
| 2007/0274934 A1 | 11/2007 | Chodorowski-Kimmes |
| 2008/0057011 A1 | 3/2008 | Ferrari |
| 2008/0318900 A1* | 12/2008 | Feltin ............................ 514/63 |
| 2011/0144208 A1 | 6/2011 | Feltin |

FOREIGN PATENT DOCUMENTS

| | | |
|---|---|---|
| CA | 2 791 252 A1 | 9/2011 |
| EP | 0 722 970 B1 | 4/1999 |
| GB | 1 347 950 | 2/1974 |
| GB | 2 048 229 A | 12/1980 |
| GB | 2 144 992 A | 3/1985 |
| WO | WO 97/36572 | 10/1997 |
| WO | WO 02/47628 A1 | 6/2002 |
| WO | WO 2008/113992 A2 | 9/2008 |

OTHER PUBLICATIONS

New Functional Materials Based on Self-Assembling Organogels: From Serendipity Towards Design**. Highlights, Angew. Chem. Int. Ed. 2000, 39, No. 13.

Selective synthesis of non-symmetrical bis-ureas and their self-assembly. Olivier Colombani and laurent Bouteiller. New J. Chem., 2004, 28, 1373-1382.

Balancing Hydrogen Bonding and van der Waals Interactions in Cyclohexane-Based Bisamide and Bisurea Organogelators. Langmuir Article. Niek Zweep, Andrew Hopkinson, Auke Meetsma, Wesley R. Browne, Ben L. Feringa, Jan H. van Esch. 2009 American Chemical Society.

Attempt toward 1D Cross-Linked Thermoplastic Elastomers: Structure and Mechanical Properties of a New System. Olivier Colombani, Chantal Barioz, Laurent Bouteiller, Corinne Chaneac, Lionel Fomperie, Frederic Lortie and Helene Montes. 2005 American Chemical Society. Macromolecules 2005, 38, 1752-1759.

Low Molecular Mass Gelators of Organic Liquids and the Properties of Their Gels. Pierre Terech, Richard G. Weiss. Chem. Rev. 1997, 97, 3133-3159. 1997 American Chemical Society.

Highly Cooperative Formation of Bis-Urea Based Supramolecular Polymers. JACS Articles. Vesna Simic, Laurent Bouteiller, Matthieu Jalabert. J. AM. Chem. Soc. 2003, 125,13148-13154.

Structural and Rheological Study of a Bis-urea Based Reversible Polymer in an Apolar Solvent. Frederic Lortie, Sylvie Boileau, Laurent Bouteiller, Christophe Chassenieux, Bruno Deme, Guylaine Ducouret, Matthieu Jalabert, Francoise Laupretre, Pierre Terech. 2002 American Chemical Society. Langmuir 2002, 18, 7218-7222.

Effects of Hydrogen Bonding and van der Waals Interactions on Organogelation Using Designed Low-Molecular-Weight Gelators and Gel Formation at Room Temperature. Masahiro Suzuki, Yasushi Nakajima, Mariko Yumoto, Mutsumi Kimura, Hirofusa Shirai, Kenji Hanabusa. 2003 American Chemical Society. Langmuir 2003, 19. 8622-8624.

Low Molecular Weight Bis-Urea Organogelators. Kimberly D. Deaton. Feb. 21, 2002.

* cited by examiner

BISUREA GELLING AGENTS AND COMPOSITIONS

CROSS REFERENCE TO RELATED APPLICATIONS

This application claims priority to U.S. Provisional Patent Application No. 61/530,045, entitled "Bisurea Gelling Agents and Compositions" which was filed on Sep. 1, 2011.

FIELD OF THE INVENTION

This invention relates to bisurea gelling agents that impart a number of unexpected benefits within various gelled formulations and exhibit great versatility in terms of gelling capabilities for many types of solvents. Such bisurea gelling agents have the following general structure:

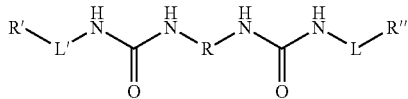

wherein R can be aliphatic chains or rings or aromatic rings; L and L' are the linking groups which may be same or different ethylene oxide or propylene oxide chains or combinations thereof; R' and R" are linear or branched alkyl groups which may be same or different. Such bisurea gelling agents should include pendant groups, such as, for example, sterically hindering alkyl groups attached to polyoxyalkylenated moieties. These pendant groups allow the gelling agent to be compatible with the target liquid system at elevated temperatures, while controlling and/or limiting the gel network formation and strength during the cooling cycle. The result is that a reliable, hard gel is formed that does not crash out of solution easily and that does not exhibit unwanted precipitating out within the final formulation. Alternatively, novel gelling agents having two urea groups that are asymmetrical in configuration have been produced in order to provide the same control in temperature, compatibility, and efficiency. Final gelled formulations, such as antiperspirant sticks and other consumer items, are provided as well within this invention.

BACKGROUND OF THE INVENTION

All U.S. patents and patent applications cited below are herein entirely incorporated by reference.

Gels are generally formed when attractions between molecules (such as via hydrogen bonding, Van der Waals forces, ionic attractions, pi-pi interactions, etc.) facilitate the formation of an extensive three-dimensional strand network that traps and/or encapsulates (i.e., immobilizes) a solvent component between such strands (such as via hydrogen bonding). Gelling agents have been utilized in various applications for many years, particularly in terms of immobilizing certain solvents, mostly polar in nature, for improvements in storage and delivery thereof. Most importantly, and particularly for consumer purposes (personal care products, cosmetics, antiperspirants, etc.), gelling agents have been prominent in permitting utilization of difficult-to-handle and/or difficult to apply beneficial solvents and active ingredients within such consumer product formulations.

Generally, the presence of gelling agents provides formulation structure which, in turn, permits a more uniform and even application of desirable additives to target surfaces (skin, for example). Without such gelled systems, the solvents and/or actives present within such formulations would most likely precipitate out of solution or bloom to the surface, thereby creating a delivery problem with either too little or too great an amount applied to the target area. In particular, certain organic solvents may provide excellent skin treatment effects, yet, due to high volatility, such materials are difficult to store and difficult to actually apply to target surfaces without losing the efficacy thereof. Solid actives (for example aluminum salts in antiperspirants) are likewise difficult to keep in a stable uniform dispersion that can be applied evenly to target surfaces (axilla of humans, for instance).

As a result, it was realized in the past that delivery and storage systems for such highly volatile solvents and solid active ingredients were required and gels and/or solids were developed in response. Over the years, improvements in certain gelling materials has led to a number of results, some of great value, and some of limited usefulness. For instance, for antiperspirant sticks, certain expensive amide-based gelling agents were produced for low residue transfer and gelling of very specific silicone-based systems, and in particular, polar formulations. Such polar formulations create certain undesirable effects, such as high dissolution temperatures, solvent incompatibility, cracking, a lack of a clear gel thereof, a "wet" feeling upon application, and a reduction in certain degrees of efficacy of the active ingredients due to the loss of certain amounts of such actives dissolved within such polar components.

The ability to control and gel non-polar solvents (such as of a certain maximum dielectric constant, for instance) is believed to provide a manner of overcoming these limitations of amide/hydroxystearic acid-based gelling systems. Although such an amide/hydroxystearic acid gel has proven effective for personal care consumer applications to a certain extent, unfortunately such systems exhibit low versatility (in terms of solely gelling polar co-solvents, for example) and high costs, thereby providing a gelling agent of limited availability and diminished demand.

Another type of gelling agents used to make low residue antiperspirant sticks is dibenzylidene alditol (DBS) based compounds. Although these gelling agents can provide hard and stable polar solvent gels (like propylene glycol, isostearyl alcohol, etc.), they generally cannot efficiently gel non-polar solvents. Furthermore, the DBS gelling agents are not acid stable, and they have limited use in antiperspirant formulations because the antiperspirant actives are acidic in nature.

Furthermore, particularly within consumer applications, many gelling agents are limited in their versatility due to incompatibility with and/or instability in the presence of certain necessary additives, including, without limitation, emollients, waxes, fillers, antimicrobial agents, fragrances and other additives. Waxes in particular have proven troublesome, within antiperspirant stick formulations due to the ability of such components to crystallize therein. Once in crystallized form, such waxes have a tendency to migrate to the surface of the antiperspirant gel and, when the gelled formulation is applied to a target surface, such crystallized waxes will invariably leave a white residue thereon. Such aesthetically displeasing results have been combated against for many years without much improvement except for the removal of certain amounts of needed wax components, which are generally added to impart firmness, structure, and other physical properties to the target gel.

Thus, there is a distinct need to provide a cost-effective gelling agent that reduces and/or controls the level of crystallinity in the waxes therein in order to create a stable, clear gel and to prevent residue generation on treated surfaces. Unfortunately, except for the aforementioned expensive amide-based types, such gelling agents have not been provided within the pertinent consumer markets. Additionally, most gelling agents are highly susceptible to oxidation and discoloration when stored, particularly those comprising highly oxidative actives. A gelling agent exhibiting stability to oxidation, pH stability (2-10), and thermal stability (12 weeks at 45° C.), in addition to other properties, is thus desirable for aesthetic and practical purposes.

Additionally, many gelling agents fail to provide sufficient levels of water/film interface durability for utilization as vehicles for skin or other surface application formulations. The ability for such formulations to be substantive upon water contact can be an absolute necessity for proper long-term skin contact applications (such as for antiperspirants, cosmetics, sunscreens, and the like) and many current gelling agents fail to provide such a characteristic. Thus, in addition to the properties noted above, there is a desire for a film fixing water-repellent, or at least a water-resistant, gelling agent for such end uses. To date, such a result has not been forthcoming, particularly in combination with the other desirable properties noted above.

Bisurea and polyurea compounds are well known as organic thickeners and have been used in the field of lubricants. Recently, bisurea gelling agents have been used to gel high boiling point non-polar solvents, and the microstructures of the three dimensional networks thus formed have been studied. However, these bisurea gelling agents have high melting temperature and dissolution temperature in the solvents, or the formed gels are not stable in ambient conditions for long periods of time (i.e., shelf life of weeks and months). Thus, new gelling agents with lower dissolution temperature and excellent gel clarity and stability are needed.

SUMMARY OF THE INVENTION

Therefore, an object of the invention is to provide a gelled solvent system comprising at least one gelling agent represented by the structure of Formula (I)

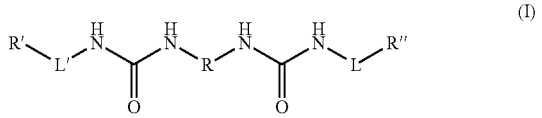

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers, wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units, and wherein the system is a pourable liquid above the dissolution temperature and the system is a stable gel below the gelling temperature. Further, the gelled solvent system of the present invention is pH stable in the range from pH=2 to pH=12.

In yet another aspect, the gelled solvent system of the present invention comprises at least about 1% of a wax component by weight and at least about 0.1% to about 20% by weight of said at least one gelling agent. In a further aspect, the gelled solvent system of the present invention comprises a fragrance, and the fragrance evaporation rate is lower than that of a solvent system without the gelling agent. In yet another aspect, the gelled solvent system of the present invention contains between about 0.001% and about 20.0% of the at least one gelling agent. In yet another aspect, the gelled solvent system of the present invention contains between about 0.001% and about 10.0% of the at least one gelling agent. In a further aspect, the gelled solvent system of the present invention contains between about 0.001% and about 5.0% of the at least one gelling agent. In another aspect, the gelled solvent system of the present invention contains between about 0.001% and about 4.0% of the at least one gelling agent. In yet another aspect, the gelled solvent system of the present invention contains between about 0.001% and about 3.0% of the at least one gelling agent.

Another object of the invention is to provide a gelled solvent system comprising at least one gelling agent represented by the structure of Formula (I)

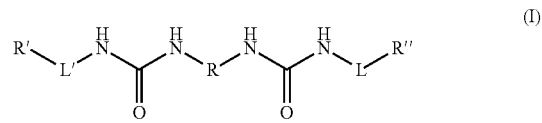

wherein R is a $C_3$-$C_{18}$ linear or branched alkylene chain or an aromatic ring; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units, and wherein the system is a pourable liquid above the dissolution temperature and the system is a stable gel below the gelling temperature.

In yet another aspect, the invention provides a gelled solvent system comprising at least one gelling agent represented by the structure of Formula (I)

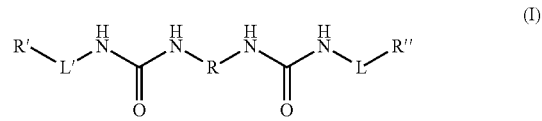

wherein R is a $C_3$-$C_{18}$ linear, branched or cyclic moiety selected from the group consisting of unsubstituted or substituted phenyl, phenyl ether, and phenyl methylene; and R' and R" may be the same or different and are selected from the group consisting of $C_1$-$C_{36}$ linear or branched alkanes, α-methyl branched $C_2$-$C_{36}$ alkanes or aryl alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units, and wherein the system is a pourable liquid above the dissolution temperature and the system is a stable gel below the gelling temperature.

In another aspect, the invention provides a gelled solvent system comprising a mixture of at least one gelling agent represented by the structure of Formula (I),

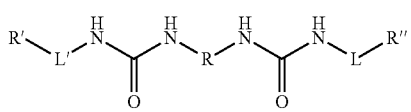

(I)

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units, and one compound represented by the structure of Formula (II) or Formula (III)

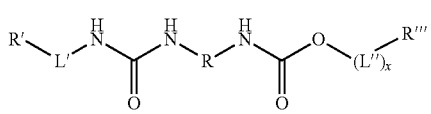

(II)

wherein R is a $C_3$-$C_{18}$ linear, branched, or cyclic moiety; and R' is selected from the group consisting of $C_2$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein L' is selected from the group consisting of ethylene oxide chains, propylene oxide chains, and mixtures thereof, and the chains may comprise one or a plurality of repeat units; wherein R''' is selected from the group consisting of H, $CH_3$, $C_2$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein x=0 or 1 and L" is selected from the group consisting of ethylene oxide chains, propylene oxide chains, and mixtures thereof, and the chains may comprise one or a plurality of repeat units,

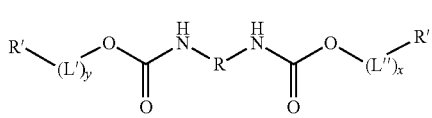

(III)

wherein R is a $C_3$-$C_{18}$ linear, branched, or cyclic moiety; and R' and R''' are selected from the group consisting of H, $CH_3$, $C_2$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein x=0 or 1 and y=0 or 1 and, L' and L" are selected from the group consisting of ethylene oxide chains, propylene oxide chains, and mixtures thereof, and the chains may comprise one or a plurality of repeat units; and wherein the system is a pourable liquid above the dissolution temperature and the system is a stable gel below the gelling temperature.

Yet another object is to provide an antiperspirant gel formulation comprising at least one gelling agent represented by the structure of Formula (I), at least one antiperspirant solvent component, and at least one antiperspirant active. Further, the antiperspirant gel formulation is clear.

Yet another object is to provide a cosmetic gel formulation comprising at least one gelling agent represented by the structure of Formula (I), at least one cosmetic solvent component, and at least one cosmetic active. Further, the cosmetic gel formulation is clear.

Yet another object is to provide a candle gel formulation comprising at least one gelling agent represented by the structure of Formula (I) and at least one candle solvent component. Further, the candle gel formulation is clear.

In yet another aspect, the invention includes a method of producing a gelled solvent system comprising the steps of: (a) introducing an already-produced gelling agent represented by the structure of Formula (I) into a solvent-containing liquid composition, (b) heating the resultant gelling agent-solvent formulation with stirring above the dissolution temperature, and (c) allowing said resultant stirred and heated formulation to cool below the gelling temperature into a stable gel.

Yet a further object is to provide a gelling agent that provides excellent gel stability, clarity, and efficiency at room temperature and over an appreciable amount of time for a variety of different types of non-polar solvents. Another object of the invention is to provide a means for producing a gelling agent that exhibits a gel temperature of at least about 20° C. and a dissolution temperature of at most about 200° C. In another aspect, the gelling agent exhibits a gel temperature of at least about 50° C. and a dissolution temperature of at most about 130° C. In yet another aspect, the gelling agent exhibits a gel temperature of at least about 70° C. and a dissolution temperature of at most about 90° C. These temperatures ranges may be most suitable for certain types of personal care products.

Yet another object of the invention is to provide a gelling agent that exhibits a gelling temperature above the wax crystallization temperature of certain types of waxes commonly present within antiperspirant and cosmetic formulations. A further object of this invention is to provide a gelled formulation made from the inventive gelling agent that exhibits a very high level of film durability on skin or other substrates. Another object of the invention is to provide a process to make the gelling agents.

DETAILED DESCRIPTION OF THE INVENTION

Definitions

The term "low residue" as used herein refers generally to the visible residue left on the applied areas of the skin during or after application, and more specifically refers to the visible residue index of the composition as defined by the methodology described hereinafter.

The term "ambient conditions" as used herein refers to surrounding conditions under about one atmosphere of pressure, at about 50% relative humidity, and at about 25° C., unless otherwise specified.

The term "substantially free" as used herein, unless otherwise specified, refers to preferred negative limitations of the compositions of the present invention, and are directed to the amount or concentration of inorganic thickening agents, organic polymeric thickening agents, dibenzylidene alditol gellants, n-acyl amino acid derivatives, or combinations thereof, in the composition. The term "substantially free" means that the compositions preferably contain less than an effective amount of such agents when used alone to provide any thickening or measurable viscosity increase to the composition. In this context, the negative limitations pertain only to those thickening or gelling agents which are also solid under ambient conditions, and which are not silicone containing materials or polymeric derivatives of 12-hydroxystearic acid. Generally, the compositions preferably contain less than 5%, preferably less than 2%, more preferably less than 1%, even more preferably less than 0.5%, most preferably zero percent, of such agents by weight of the composition. Examples of inorganic thickening agents to which the above-described negative limitations pertain include finely divided or colloidal silicas, fumed silicas, and silicates, which includes montmorillonite clays and hydrophobically treated montmorillonites, e.g., bentonites, hectorites and colloidal magnesium silicates. Examples of organic polymeric gelling agents to which the above-described negative limitations pertain include organic polymers well known in the antiperspirant or personal care art for use in providing gelling or thickening or other physical or aesthetic benefits to a composition, specific examples of which include hydrogenated butylene/ethylene/styrene copolymer, polyethylene, oxidized polyethylene, polyamides, acrylic acid polymers, ethylene acrylate copolymers, and other organic polymeric gelling agents described in Rheological Properties of Cosmetics and Toiletries, Edited by Dennis Laba, published by Marcel Dekker, In., New York (1993), which description is incorporated herein by reference.

The terms "alkyl" and "alkenyl" as used herein, unless otherwise specified, refer to substituted or unsubstituted, branched, cyclic or linear, hydrocarbons having from 1 to about 22 carbon atoms.

The term "aliphatic," as used herein, unless otherwise specified, refers to substituted or unsubstituted, branched, cyclic or linear, hydrocarbons having from 1 to about 60 carbon atoms.

The term "volatile" as used herein refers to materials which have a vapor pressure under ambient conditions of at least about 0.2 mm of Hg. Conversely, the term "non-volatile" as used herein refers to materials which have no measurable vapor pressure or which have a vapor of less than about 0.2 mm of Hg under ambient conditions.

As used herein, the articles including "the", "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

Bisurea Gelling Agents

This invention encompasses a bisurea gelling agent represented by the structure of Formula (I)

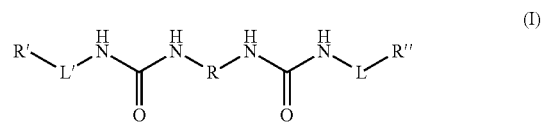

wherein R is a $C_3$-$C_{18}$ linear, branched, or cyclic moiety; in one aspect, R is a $C_3$-$C_{18}$ linear or branched alkylene chain or an aromatic ring; in another aspect, R is a $C_3$-$C_{18}$ linear, branched or cyclic moiety selected from the group consisting of unsubstituted or substituted phenyl, phenyl ether, phenyl methylene, and the like; and R' and R" may be the same or different and are selected from the group consisting of $C_2$-$C_{36}$ linear or branched alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units; and wherein said gelling agent is present as a distinct solid compound at room temperature without any gelled solvent present therewith.

Another invention encompassed herein is a gelling agent conforming to the structure of Formula (I), above, that exhibits a gel temperature of at least 20° C. and a dissolution temperature of at most 200° C. in a non-polar solvent. Also encompassed within this invention is a gelled solvent system comprising at least one gelling agent represented by the structure of Formula (I) above. The gelled solvent system may be further characterized as being a clear gelled solvent system, as may be determined by refractive index values. Further encompassed within this invention is a gelled solvent system as described herein, wherein the system comprises at least 1% of a wax component by weight therein, and at least 0.1% to 20% by weight of at least one gelling agent. In another aspect, this invention includes a gelled solvent system as described above, wherein the system comprises at least 5% of a wax component by weight therein, and at least 0.5% to 10% by weight of at least one gelling agent.

Suitable waxes or wax-like materials generally have a melting point range of 30° C. to 120° C. and generally include animal waxes, plant waxes, mineral waxes, silicone waxes, synthetic waxes, and petroleum waxes. Exemplary waxes include ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, cetyl esters, hydrogenated jojoba oil, hydrogenated jojoba wax, hydrogenated microcrystalline wax, hydrogenated rice bran wax, japan wax, jojoba butter, jojoba esters, jojoba wax, mink wax, montan acid wax, ouricury wax, PEG-6 beeswax, PEG-8 beeswax, rice bran wax, spent grain wax, sulfurized jojoba oil, synthetic beeswax, synthetic candelilla wax, synthetic carnauba wax, synthetic japan wax, synthetic jojoba oil, stearoxy dimethicone, dimethicone behenate, stearyl dimethicone, synthetic homo- and copolymer waxes of ethylene and/or propylene, fluorinated wax, or mixtures thereof. The wax may be included in the gelled solvent system in an amount from 1% to about 40% by weight, or in an amount from 5% to about 30% by weight, or in an amount from 10% to 30% by weight.

Additionally encompassed is a method of producing a gelled solvent system comprising the introduction of an already-produced gelling agent conforming with the structure of Formula (I) into a solvent-containing liquid composition, heating the resultant gelling agent-solvent formulation with stirring until dissolution of the gelling agent occurs, and allowing said resultant stirred and heated formulation to cool into a stable gel. Further encompassed within this invention is an antiperspirant gel formulation comprising at least one gelling agent as defined above, at least one antiperspirant solvent component, and at least one antiperspirant active, as well as a cosmetic gel formulation comprising at least one gelling agent as defined above, at least one cosmetic solvent, and at least one cosmetic active. This invention also provides processes to make such gelling agents.

Such an inventive gelling agent and gelled solvent system have heretofore not been provided within the gelling agent and gelled solvent system industries. It has been found that such bisurea gelling agents provide a number of benefits within the target markets, most notably the ability to reduce the crystallinity of wax compounds present therein, thereby reducing the undesirable potential for white residue left on surfaces to which such gelled formulations are applied. Furthermore, such gelling agents can be introduced in very low levels and still provide excellent gelation for certain classes of solvents. For manufacturing improvements, such gelling agents exhibit low dissolution temperatures, thereby permitting more cost-effective energy levels to be utilized for lower temperature manufacturing of target gelled solids. Such gelling agents also exhibit low gel temperatures for certain solvent classes, thereby permitting lower temperatures to be utilized to effectuate proper gelling results therewith. It has also been found that such gelling agents (a) permit production of stable clear, non-polar solvent gels, (b) create a desirable change in the refractive index of certain oil components (such as the types generally added within gelled cosmetic and/or antiperspirant formulations for skin treatment benefits) in order to provide such clear properties therein, and (c) exhibit an ability to change the physical properties of wax additives present within such gelled formulations in order to provide the needed stability, clarity, and ultimate low level of residue generation on treated surfaces. Such desirable characteristics shall be discussed in greater detail below.

The gelling agent and formulations of the current invention have been found, unexpectedly, to meet all of the benefits desired of such materials, particularly in the presence of certain non-polar solvents and potentially oxidative and/or acidic or basic solid cosmetic and/or antiperspirant active compounds.

The importance of the structure of the present gelling agent lies, in one manner, in the ability to control and/or limit intermolecular stacking to form crystalline phase during storage. Thus, the resultant gel will not exhibit undesirable crystals precipitating out from the gel and, furthermore, will not exhibit syneresis or residue formation. The presence of either two polyoxyalkylene chains (in the L and L' positions), and thus the presence of α-methyl branched $C_2$-$C_{18}$ ethers or β-methyl branched $C_2$-$C_{18}$ ethers thereon, provides sufficient steric hindrance to control, tune, or prevent unwanted hydrogen bonding and close and tight intermolecular stackings between individual gelling compounds when in gelled state. Furthermore, the presence of different groups in the R' and R" positions also provides the needed steric hindrance to prevent such undesirable precipitation results. These needed structures also provide, through the aforementioned steric hindrance capabilities, the potential to prevent hydrogen bonding to the extent that the desired gel temperatures and nonpolar solvent dissolution temperature can be met in order to permit proper introduction and overall stability of solvents and active solids within the target gelled system itself. The dissolution temperature of the bisurea gelling agent is less than that of the decomposition temperature of the target nonpolar solvent, thereby permitting desirable low temperature gel production without losing a substantial amount of the needed gelled solvent therefrom.

Furthermore, such a structure accords higher gel temperatures than the wax crystallization temperatures of such wax fillers generally present within cosmetic stick formulations for physical property improvements. As noted above, it has been found that, within personal care formulations, and specifically within antiperspirant sticks, the presence of high degrees of crystalline waxes (which are, again, needed additives for physical property purposes) leave large amounts of white residue on the target contacted surface. Such transferred crystalline waxes also appear to contribute to long-term discoloration of either the surface itself or other substrates that come into contact with such a residue-covered surface (clothing, in particular, white or light-colored clothing, which may turn yellowish in color after exposure, for example). The ability to reduce the formation of crystalline waxes (and thus the ability to retain the amorphous structure of such components) is thus necessary to prevent such residue formation and ultimate discoloration results. Since the bisurea gelling agents actually exhibit higher gel temperatures than the wax crystallization temperature(s) of standard wax components, the result is a gel that forms at a temperature at which the wax components remain amorphous in nature, thereby reducing the extent of crystallization of the waxes and the propensity for residue formation as noted above.

One important property exhibited by such an inventive bisurea gelator is the increased film viscosity and interface adhesion which provides a wet barrier (and thus the exhibition of substantial water insolubility). As a result, the ability to adhere the delivered gelled solvents and other additives to certain target surfaces, such as, as one non-limiting preferred example, human skin, for long-term application is a substantial benefit heretofore not accorded by other gelling agents. Due to such high levels of interface adhesion, such gelled compositions will remain readily adhered to the target surface unless a good solvent or high temperature is directly contacted therewith. Thus, the gelled solvent system comprising the gelling agent of the present invention is water resistant and has superior adhesion properties. With a sunscreen composition, as another non-limiting example, the ability to provide gelled skin ultraviolet protectants to a target skin surface within a water-insoluble composition would thus permit application thereof without a need for re-application in relatively short time intervals, particularly when the user is present outside or near or within an aquatic environment. Thus, in addition to cosmetic stick applications, other, less rigid possibilities for these inventive gelling agents and compositions made therewith include, without limitation, sunscreens, etc.

Also, such bisurea gelling agents have the ability to gel non-polar solvents in such a way as to increase film viscosity and/or film interface adhesion. The intrinsic nature of such gelling agents, particularly where the R' and R" groups of Formula (I) are of the same type, imparts such a film property, thereby allowing for utilization within end-uses wherein long-term application (without fear of removal by exposure and/or contact with water) is needed (such as in suntan lotions, hair dyes, teeth whiteners, and the like).

Methods of Making Bisurea Gelling Agents

The inventive bisurea gelling agents can be made by reacting diisocyanates with primary amines in an appropriate solvent. The diisocyanates can be aliphatic or aromatic. Examples of aliphatic diisocyanates include, without limitation, 1,4-diisocyanatobutane; 1,6-hexamethylene diisocyanate (HDI); 1,8-diisocyanatooctane; 1,12-diisocyanatododecane; 1,5-diisocyanato-2-methylpentane; isophorone diisocyanate (IPDI); 1,3-bis(isocyanatomethyl)benzene (m-xylene diisocyanate); 1,3-bis(1-isocyanato-1-methylethyl)benzene (TMXDI); cyclohexylene diisocyanate; bis(4-isocyanatocyclohexyl)methane (HMDI); trimethyl-1,6-diisocyanatohexane; and mixtures thereof.

Examples of aromatic diisocyanates include, without limitation, 2,4-diisocyanatotoluene (2,4-TDI); 2,6-diisocyantotoluene (2,6-TDI); tolylene 2,5-diisocyante; 4,4'-diisocyantato-diphenylmethane; α,4-tolylene diisocyante; α,α-dimethyl-α,4-phenyl diisocyanate; 4-bromo-6-methyl-1,3-phenylene diisocyanate; 1-chloromethyl-2,4-diisocyanatobenzene; 4-chloro-6-methyl-1,3-phenylene diisocyanate; 3,3'-dimethoxy-4,4-biphenylene diisocyanate; 3,3'-dimethyl-4,4'-biphenylene diisocyanate; 1,3-phenylene diisocyanate; 1,4-phenylene diisocyanate; naphthalene-1,5-diisocyanate (NDI); and mixtures thereof.

Suitable primary amines preferably have one or more ether linkages in the main hydrocarbon backbone. For example, the ether amines from Tomah having the general structure $ROCH_2CH_2CH_2NH_2$ or $ROCH_2CH_2CH_2NHCH_2CH_2CH_2NH_2$ (wherein R is a linear or branched alkyl chain) can be used. Specifically, the ether amines may include, without limitation, PA-10 (isohexyloxypropylamine), PA-12 EH (2-ethylhexyloxypropylamine), PA-1214 (octyl/decyloxypropylamine), PA-14 (isodecyloxypropylamine), PA-16 (isododecyloxypropylamine), PA-17 (isotridecyloxypropylamine), PA-19 ($C_{12-15}$ alkyloxypropylamine), DA-14 (isodecyloxypropyl-1,3-diamonopropane), DA-16 (isododecyloxypropyl-1,3-diaminopropane) and DA-17 (isotridecyloxypropyl-1,3-diaminopropane).

Another example of the primary amines is the Tomadol™ PA series polyether amines from Tomah having the general structure $RO(CH_2CH_2O)_nCH_2CH_2CH_2NH_2$ (wherein R is a linear or branched alkyl radical). Other classes of primary amines which may be suitable include the Jeffamine® amines and Surfomamine® from Huntsman. Specific examples of these include Surfomamine® ML-300, Surfomamine® 1000, Jeffamine® M-600, and Jeffamine® M-300.

The bisurea gelling agents of this invention may be made using various types of organic solvents or water which are compatible with isocyanates and primary amines. The solvents may be aromatic liquids such as, for example, benzene, toluene, xylene, and the like. Other suitable solvents include, for example, methanol, ethanol, hexane, acetone, and the like. Water may also be used in the process as reaction media.

By using solvents which are not reactive to either isocyanates or primary amines, the reactants and solvents can be mixed together at temperatures in the range of about −80° C. to about 100° C. for a certain length of time until the reaction is completed. If the products precipitate out from the reaction media, they can be filtered, washed and dried. If the products are soluble in the solvents, non-solvent liquids, such as water, may be added to precipitate out the products. In the case of water as reaction solvent, primary amines and water can be mixed together first in the reaction flask and kept at an appropriate temperature. The isocyanates may then be added in a controlled manner to minimize the contact between isocyanate and water and their reaction side-product.

Organic Gels Containing Bisurea Gelling Agents

Unless otherwise indicated, all parts and percentages are by weight and conditions are ambient, i.e. one atmosphere of pressure and 25° C. The gelled composition of the present invention is basically the result of a mixture of (a) an organic liquid capable of being gelled by a bisurea gelling agent as defined by Formula (I) and (b) a bisurea gelling agent as defined by Formula (I).

The concentration of the bisurea gelling agent, or gelator, in the final gelled composition is about 0.1 weight % or greater. Concentrations of the bisurea gelator as high as 40 wt. % or more may be employed, but these amounts approach the upper limit of solids concentration, viscosity and stability. In one aspect, the concentration of bisurea gelator ranges from about 0.1 weight % to about 40 weight %, and in another aspect, from about 1 weight % to about 30 weight %, from about 1 weight % to about 20 weight %, based on the weight of the final gelled composition.

The versatility of such a gelator is shown by the breadth of different types of solvents such a compound may gel. Organic liquids, preferably, though not necessarily non-polar in nature, useful in the present invention are organic compounds and mixtures of organic compounds which are liquid at dissolution conditions, and which are capable of being gelled by such bisurea gelators. Certain polar types may also be gelled, depending on the R' and R" groups present on the target bisurea gelator. Generally, organic liquids (being either polar or non-polar in nature) in which the inventive bisurea gelator exhibits a solubility of greater than about 0.1 g per 100 g of solvent when heated, but is substantially less soluble in the solvent when cooled, are capable of being gelled. Virtually all common organic solvents which meet the aforementioned criteria may be employed. More particularly, these liquids include, without limitation, any of the classes listed below, and any combinations of liquids within each class or different types within different classes: low hydrogen bonding non-polar liquids exhibiting dielectric constants less than 3, non-polar liquids exhibiting dielectric constants less than 6 minus activated hydrogen, aliphatic or aromatic ethers (such as, as non-limiting examples, myristyl ether derivatives, polypropylene glycol-3 myristyl ether, and polypropylene glycol-14 butyl ether), aliphatic or aromatic hydrocarbons (such as, as non-limiting examples, mineral oils, polydecene, paraffins, and isoparaffins), aliphatic or aromatic esters (such as, as non-limiting examples, isopropyl myristate, lauryl myristate, isopropyl palmitate, diisopropyl sebacate, diisopropyl adipate, and fatty alkyl benzoates), aliphatic or aromatic alcohols (such as, as non-limiting examples, stearyl alcohol, isostearyl alcohol, and octyl dodecanol), aliphatic mono- or poly-glycerides, alkanes, polyolefins, cyclic or linear silicones, oxyalkylatealkyl esters or ethers, saturated or unsaturated vegetable oils, aliphatic or aromatic amines, aliphatic or aromatic amides, aliphatic or aromatic acids, and terpenes (such as, as one non-limiting example, d-limonene), and mixtures thereof.

By way of example, more specific organic liquids may be selected from acetone, acetophenone, aniline, benzene, benzyl alcohol, n-butanol, carbon tetrachloride, castor oil, chlorobenzene, chloroform, coconut oil, cyclohexanone, dioctylphthalate, dioxane, epoxy resin (BPA type), ethanol, ethyl acetate, ethylene glycol, methyl ethyl ketone, nitrobenzene, octanol, propylene glycol, pyridine, tetraline, toluene, whale oil, xylene and liquid petroleum products, such as automotive and aviation fuel, fuel oil, illuminating oil, solvents (e.g. mineral spirits), lubricants, asphalts, cable oil and cutting oil, and mixtures thereof, as a non-exhaustive list.

Non-polar organic liquids, such as non-polar solvents, which can be gelled by the process of the present invention are generally almost any of those which have a dielectric constant of less than about 15.0. In one aspect, non-polar organic liquids, such as non-polar solvents, are those which have a dielectric constant of less than about 10 and a solubility parameter less than about 9 and which have a solubility less than about 10% by weight in water. In another aspect, the non-polar organic liquid, such as a non-polar solvent, may have a dielectric constant of less than 5.0, or even of less than 4.0. Suitable examples of such non-polar organic liquids include petroleum hydrocarbons such as gasoline, naphtha, kerosene, gas oil, heavy oil and crude oil; lubricating oils such as spindle oil and turbine oil; liquid paraffin, pure hydrocarbons such as benzene, xylene, toluene, hexane, heptane, octane, and cyclohexane; esters such as butyl acetate, amyl acetate, diethyl phthalate, dibutyl phthalate, dioctyl phthalate, diethyl sebacate and dioctyl sebacate; ketones such as methyl isobutyl ketone and diisobutyl ketone; aldehyde such as anisaldehyde; chlorinated hydrocarbons such as carbon tetrachloride, tetrachloroethylene and chlorobenzene; phosphoric esters such as tributyl phosphate and tricresyl phosphate; normally liquid polyoxyalkylene monoalkyl ethers such as polyoxyethylenemonolauryl ether containing 4 to 6 oxyethylene units, polyoxypropylene mono $C_4$ to $C_{12}$ alkyl ether containing 10 to 50 oxypropylene units such as polyoxypropylene mono butyl ether, polyoxypropylene mono lauryl ether; normally liquid polyoxypropylene mono lauryl ether; normally liquid polyoxyalkylene glycol fatty acid esters, such as polyoxyethylene glycol lauric or oleic acid ester containing 4 to 6 oxyethylene units; fatty oils such as corn oil, soybean oil, olive oil, rape seed oil, cotton seed oil, sardine oil, herring oil and whale oil; silicone oil, mixtures thereof and liquids containing predominantly these non-polar organic liquids. On the other hand, organic liquids having a dielectric constant greater than about 10, such as acetone and ethanol, and having a solubility more than 10% by weight in water such as acetic acid and butyric acid do not gel satisfactorily.

In addition, non-polar organic liquids which can be gelled to produce a clear gel by the process of the present invention are generally almost any of those which have a dielectric constant of less than about 5 and are aprotic at concentration of gelling agent in the range of about 0.001 to about 2%. Further, clear gels may be produced from non-polar solvents which have a dielectric constant greater than about 5 using a concentration of gelling agent greater is than about 2%.

The non-polar organic liquids may contain other ingredients as may be desired to achieve special effects. An emulsion or suspension of the non-polar organic liquid with water may be gelled. In the case of a system which forms a water-in-oil type emulsion or suspension wherein the water content is below 50%, the entire system may be gelled. And, in the case of a system which forms an oil-in-water type emulsion or suspension, the non-polar organic component may be gelled as an aggregate.

Antiperspirant Compositions

For antiperspirant compositions, one particularly preferred class of organic liquids to be gelled or co-gelled are silicones. Such materials provide excellent skin compatibility and other benefits (such as moisturizing, soothing, cooling, and the like). Within this class of organic liquids, the following potentially preferred types of silicones include a modified or organofunctional silicone carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof. These modified silicone carriers must be liquid under ambient conditions, and have a viscosity of less than about 100,000 centistokes, preferably less than about 500 centistokes, more preferably from about 1 centistoke to about 50 centistokes, and even more preferably from about 1 centistoke to about 20 centistokes. These modified silicone carriers are generally known in the chemical arts, some examples of which are described in 1 Cosmetics, Science and Technology 27-104 (M. Balsam and E. Sagarin ed. 1972); U.S. Pat. No. 4,202,879 to Shelton; U.S. Pat. No. 5,069,897 to Orr. These publications are incorporated herein by reference.

More specifically, the modified silicone carriers suitable for use in the antiperspirant gel-solid stick compositions include, but are not limited to, compounds or materials as defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu, e.g. Japanese Patent Publication JP86143760 or from Walker Chem. 6 MBH (described in EP722970); alkoxysiloxanes; alkoxysilanes; methicones (polymethylalkylsiloxanes); and combinations thereof.

Nonlimiting examples of commercially available modified silicone carriers for use in the antiperspirant gel-solid stick compositions of the current invention include the following modified silicones available from Dow Corning: DC-556 Cosmetic Grade Fluid (phenyl trimethicone); DC-704 Diffusion Pump Fluid (Tetramethyl-Tetraphenyl-Trisiloxane);

DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318-Fluid (Cyclomethicone [and] Vinyldimethicone); DC-QF1-3593A fluid (Trimethylsiloxysilicate) and combinations thereof.

Other nonlimiting examples of commercially available modified silicone carriers for use in the antiperspirant gel-solid stick compositions of the current invention include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate) and combinations thereof.

Other nonlimiting examples of commercially available modified silicone carriers for use in the antiperspirant gel-solid stick compositions of the current invention include the following modified silicones available from Goldschmidt: Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers) and combinations thereof.

Other nonlimiting examples of commercially available modified silicone carriers for use in the antiperspirant gel-solid stick compositions of the current invention include the following: Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-711, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris[tributoxysiloxy]methylsilane); silicone copolymer F-754 (dimethicone copoly from SWS Silicones); and combinations thereof.

An anhydrous liquid carrier may be included in the antiperspirant composition and preferably comprises a volatile silicone carrier. These volatile silicone carriers may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91:27-32 (1976), which descriptions are incorporated herein by reference. Preferred among these volatile silicones are the cyclic silicones having from about 3 to about 7 silicon atoms, and more preferably from about 4 to about 5 silicon atoms. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-I 173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

The anhydrous liquid carrier may also comprise a non-volatile silicone carrier other than or in addition to the preferred modified silicone carriers previously described. These non-volatile silicone carriers are preferably linear silicones generally exhibiting viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G. E. Silicones); Velvasil and Viscasil (available from General Electric Co.); and Silicone L45, Silicone L530, Silicone L-531 (available from Union Carbide), and Siloxane F-221 and Silicone Fluid SWS-101 (available from SWS Silicones).

The anhydrous liquid carrier may further comprise, but is preferably substantially free of, organic, water-immiscible, liquid carriers or solvents. It has been found that the antiperspirant and deodorant efficacy of the gel-solid stick compositions are improved by minimizing or eliminating the amount of polar, organic, water-immiscible, liquid carriers or solvents in the composition. In this context, the term "substantially free" means that the gel-solid stick compositions preferably contain less than about 7% by weight of an organic, water-immiscible, polar liquid carrier or solvent, and more preferably less than about 3%, and even more preferably zero percent, by weight of an organic, water-immiscible, polar liquid carrier or solvent. These polar solvents are liquid under ambient conditions and include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof, provided that such solvents are also water-immiscible liquids under ambient conditions. Examples of some anhydrous liquid, water-immiscible, polar organic liquid carriers or solvents are described in Cosmetics, Science, and Technology, Vol. 1, 27-104, edited by Balsam and Sagarin (1972); U.S. Pat. No. 4,202,879 to Shelton; and U.S. Pat. No. 4,816,261 to Luebbe et al., which descriptions are incorporated herein by reference.

The anhydrous liquid carrier may comprise anhydrous, water-miscible, polar organic liquid carriers or solvents, examples of which include short chain alcohols such as ethanol. These and other polar organic carriers or solvents can be used as co-solvents for the solid non-polymeric gellant component of the antiperspirant gel-solid stick compositions of the current invention. Non-limiting examples of polar co-solvents suitable for use herein are described in U.S. Pat. No. 5,429,816 to Hofrichter et al. Other suitable polar co-solvents include those described hereinabove, which are preferably water-immiscible organic solvents, and other co-solvents such as phthalate co-solvents, benzoate co-solvents, cinnamate esters, secondary alcohols, benzyl acetate, phenyl alkane and combinations thereof.

The anhydrous liquid carrier may comprise other non-polar carriers such as mineral oil, petrolatum, isohexadecane, isododecane, various hydrocarbon oils such as the Isopar or Norpar series available from Exxon Corp. or the Permethyl series available from Persperse, and any other polar or non-polar, water-miscible, organic carrier liquid or solvent known or otherwise safe and effective for topical application to human skin.

In a preferred embodiment, the composition of the organic liquid and bisurea-gelator compound is used as a concentrate in the manufacture of cosmetic sticks (such as antiperspirants, lipsticks, and the like). Within this product group, solid antiperspirant sticks have become especially popular among consumers. These antiperspirant sticks comprise a solid matrix within which the antiperspirant active material is contained. The active can be solubilized in a liquid carrier comprising water, glycols and/or other alcohols, or maintained within a solid matrix as dispersed solids in an anhydrous system. The solid sticks which contain dissolved active often provide some low residue performance, but tend to be wet or sticky during and immediately after application to the skin, and more importantly, are often not as effective in providing antiperspirant and deodorant performance as solid sticks containing dispersed particulate active. Although the antiperspirant sticks that contain particulate actives are more effective, they also tend to leave more visible residue on the skin.

There have been many attempts at producing anhydrous antiperspirant sticks which contain dispersed particulate antiperspirant active, and which also provide improved efficacy and low residue performance during and after application to the skin, or which otherwise provide product clarity prior to (as a packaged product) or after such application (as a clear or low-residue film on the skin). One such attempt involves the combination of particulate antiperspirant active, gellants and liquid carrier in a gel stick, wherein all such components in the combination have matching refractive indices. Refractive index matching allows for more passage of light through the gel stick with less scattering of the light, thus resulting in products which appear more clear or translucent as a packaged composition or when initially applied topically to the skin. These gel sticks, however, are expensive to make due to the cost of using raw materials having only select matching refractive indices. These compositions are also very difficult to formulate given that refractive index matching for a system comprised of three or more components (e.g. particulate active, solvents and gellant) is extremely difficult and greatly limits the materials that can be used to prepare such a formulation.

Another attempt at making low residue antiperspirant sticks involves the use of gellants such as dibenzylidene alditols. These gellants, however, like many other gellants known in the art, are not acid stable and therefore tend to interact with the antiperspirant active due to the acidic nature of the active. This interaction can result in reduced efficacy of the active, poor gel formation; and lower gel stability over extended periods during shipping or storage. This interaction may also cause processing difficulties at the temperatures and holding times often used during the formulation and manufacturing process. These gellants are also commonly used in combination with glycol carriers or other solvents which tend to be wet and sticky and irritating to the skin.

Yet another attempt at making low residue antiperspirant sticks involves the use of residue masking agents such as non-volatile paraffinic hydrocarbon fluids, phenyl trimethicone, low melting point waxes and combinations thereof. These agents are used in combination with stearyl alcohol or other high residue waxes commonly used in solid antiperspirant sticks. These agents help reduce visible residue during and immediately after application of the solid stick to the skin, but also tend to be associated with an oily or sticky skin feeling during application. Moreover, although the visible residue is reduced in such compositions, there remains a visible residue on the skin when used in combination with high residue waxes such as stearyl alcohol, and this reduced residue is still more visible or apparent than the topical residue left by antiperspirant sticks which contain solubilized antiperspirant active.

One method of making low residue antiperspirant sticks is described in U.S. Pat. No. 5,429,816 to Hofrichter et al., which is hereby incorporated by reference. The antiperspirant sticks provide low visible residue during and immediately after application to the skin, and are physically and chemically stable over extended periods of time. The improved antiperspirant sticks comprise a dual gellant system having a primary gellant such as 12-hydroxystearic acid or esters or amides thereof and a secondary gellant such as n-acyl amino acid derivatives. Formation of such an antiperspirant stick with such a dual gellant system has been characterized as a "gel-solid" antiperspirant stick. An antiperspirant gel-solid, such as that described by Hofrichter et al., is an antiperspirant stick having a three-dimensional, non-polymeric, gel network in which solvent is contained or trapped. These gel-solids are typically formed by solubilizing the gellant in the solvent at temperatures above the melting point of the gellant and at temperatures at which the melted gellant is soluble in the solvent. The composition is then cooled to form the desired gel-solid composition. The low residue gel-solids described by Hofrichter et al. are remarkably stable, both physically and chemically, and will maintain the desired product hardness over an extended period of time. The gel-solids described by Hofrichter et al., however, are limited to select dual gellant systems and do not include or otherwise describe any method of making a low-residue antiperspirant gel-solid stick containing any other gellant or gellant system.

It has now been found that other low-residue gel-solids can be formulated without reliance upon the select combination of gellants described by Hofrichter et al. The composition should be substantially free of inorganic or polymeric thickening or gelling agents, and does not require refractive index matching of the particulate antiperspirant active, solid non-polymeric gellant, and anhydrous liquid carrier to obtain low residue performance. In one aspect, the compositions comprise gellant crystalline particles having an average particle size of less than about $1\mu$, and/or an elongated particle morphology defined by an aspect ratio of greater than about 2.

It has been found that the antiperspirant gel-solid stick compositions of the present invention can provide low residue performance without the need to use solubilized antiperspirant active, and without reliance upon select low residue gellants, such as, for example, dibenzylidene alditols or select gellant combinations containing n-acyl amino acid derivatives. This is accomplished primarily by providing a gelling agent that exhibits, as noted above, a gel temperature above the crystalline temperature exhibited by the wax components present therein. Thus, the composition will gel prior to the crystallization (at least to an appreciable extent) of such waxes, leaving the ultimate gel with the same basic physical properties as those including crystalline waxes therein, but without any propensity to transfer any waxy white residue to surfaces contacted therewith.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Antiperspirant gel-solid stick compositions encompassed within the present invention are characterized in terms of product hardness, visible residue index, and thermal stability. Each of these characteristics is defined in accordance with the methodologies and other limitations described hereinafter.

a) Hardness

The antiperspirant gel-solid stick compositions of the present invention have a product hardness of from about 100 gram-force to about 1000 gram-force, preferably from about 200 gram-force to about 800 gram-force, more preferably from about 250 gram-force to about 600 gram-force.

The term "product hardness" as used herein is the maximum force required when moving a penetration probe a specified distance and at a controlled rate into an antiperspirant gel-solid stick composition under the following test conditions. Higher values represent harder product, and lower values represent softer product. These values are measured at 25° C. and 15% relative humidity, using an in-house made instrument similar to TA-XT2 Texture Analyzer (Texture Technology Corp.) with some modification. The product hardness value as used herein represents the amount of force required to move a diameter 2.5 mm penetration stainless steel probe through the composition for a distance of 10 mm at a rate of 1 mm/second with 5.62 lb load cell.

b) Residue

The antiperspirant gel-solid stick compositions of the present invention have a visible residue index (the test method is described below) of from about 3 to about 20 L-value, preferably from about 3 to about 15 L-value, and more preferably from about 3 to about 10 L-value. The term "visible residue index" as used herein refers generally to the extent to which the composition of the present invention is visibly apparent as a thin topical film after application to the skin, and more specifically refers to visible residue values (expressed as an L-value on the L, a, b color scale) as measured in accordance with the following methodology, performed at 25° C., under atmospheric pressure, and at 15% relative humidity on antiperspirant stick compositions having a product hardness of from about 200 gram-force to about 600 gram-force.

A piece of black fabric, approximately 10 cm×30 cm, is attached to a movable horizontal slide which is movably attached or fixed to a larger mechanical unit. An example of a suitable piece of black fabric for use herein is dark gray Milliken Kodiak automotive fabric coated with PT5000 polyether polyurethane film from Deerfield Urethane. An antiperspirant stick composition contained within and partially extending out about 0.5 cm from a conventional package or container is positioned perpendicular to and above the attached piece of fabric, such that the product extending out of the package or container is facing the piece of fabric and the surrounding package is positioned away from the piece of fabric. The surrounding package is positioned in place using a mechanical arm or other device suitable for applying the requisite movement to the product as described herein.

The antiperspirant stick composition is then slowly moved toward and allowed to gently contact the attached piece of black fabric. A 1,000 gram weight is placed on the product sample so that the product continuously contacts the piece of black fabric during testing. The weighted sample is then moved repeatedly back and forth across the piece of fabric at a fixed speed (about 100 mm/minute), and with a fixed amount of applied pressure provided by the weighted product until the about 0.75 grams of the antiperspirant stick composition is evenly applied over a 5×20 cm area of the piece of black fabric. The piece of fabric is then carefully removed from the apparatus.

A calibrated meter (X-Rite Spectrodensitometer Model 938) is then used to measure the L-value (on the L,a,b color scale defined by CIE) of the applied surface area with D65 10 degree light source. The fabrics were measured 5 times and the averages were taken as the measured L-value.

It has been found that there is a correlation between the visible residue index range defined herein and the average wax crystallinity level of the gel composition in the antiperspirant gel-solid stick composition of the present invention. Generally, as the average wax crystallinity level in the composition decreases, low residue performance improves. In particular, it has been consistently found that a visible residue index of from about 11 to about 30 L-value corresponds to a gel temperature below the wax crystallization temperature thereof.

c) Thermal Stability

The antiperspirant formulations must have good thermal stability to survive the normal storage and selling shelf conditions for a reasonable time. The antiperspirants of this invention were tested in the laboratory to make sure they meet the stability requirements. The formulated antiperspirant about 5 gram was placed in a glass jar. This glass jar was put in the 45° C. oven and was observed over time up to 3 months. If there were no observable changes (phase separation, cracks, color change etc.) for the sample, the antiperspirant sample was labeled as "pass" for thermal stability.

The antiperspirant gel-solid stick compositions of the present invention comprise particulate antiperspirant active suitable for application to human skin. These particulate actives must remain substantially unsolubilized as dispersed or precipitated solids in the anhydrous or substantially anhydrous systems as described herein. The concentration of particulate active in the composition should be sufficient to provide the desired perspiration wetness and odor control from the antiperspirant gel-solid stick formulation selected.

The antiperspirant gel-solid stick compositions of the present invention preferably comprise particulate antiperspirant active at concentrations of from about 0.5% to about 60% by weight of the composition and more preferably from about 5% to about 35% by weight of the composition. These weight percentages are calculated on an anhydrous metal salt basis exclusive of water and any complexing agents such as glycine, glycine salts, or other complexing agents. The particulate antiperspirant active as formulated in the composition are in the form of dispersed solid particles having a preferred average particle size or diameter of less than about 100μ, more preferably from about 15μ to about 100μ, even more preferably from about 20μ to about 100μ. Also preferred are dispersed solid particulates having an average particle size or diameter of less than about 2μ, even more preferably of less than about 0.4μ. It has been found that antiperspirant active particles within the preferred particle size ranges provide lower visible residue performance from the gel-solid compositions than other less preferred particle size ranges.

The antiperspirant active for use in the antiperspirant gel-solid stick compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant gel-solid stick compositions include those which conform to the formula:

$$Al_2(OH)_aCl_b \ldots xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692 to Gilman; U.S. Pat. No. 3,904,741 to Jones et al.; U.S. Pat. No. 4,359,456 to Gosling et al.; and British Patent Specification 2,048,229 to Fitzgerald et al. All publications are incorporated herein by reference. Mixtures of aluminum salts are described in British Patent Specification 1,347,950 to Shin et al., which description is also incorporated herein by reference.

Preferred zirconium salts for use in the antiperspirant gel-solid stick compositions include those which conform to the formula:

$$ZrO(OH)_{2-a}Cl_a \ldots xH_2O$$

wherein a is from about 1.5 to about 1.87; x is from about 1 to about 7; and wherein a and x may both have non-integer values. These zirconium salts are described in Belgian Patent No. 825,146 to Schmitz, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above-described formulas. Such ZAG complexes are described in U.S. Pat. No. 3,679,068 to Luedders et al.; Great Britain Patent Application No. 2,144,992 to Callaghan et al.; and U.S. Pat. No. 4,120,948 to Shelton; all of which are incorporated herein by reference.

The antiperspirant gel-solid stick compositions of the present invention can also be formulated to comprise other dispersed solids or other materials in addition to or in place of the particulate antiperspirant active. Such other dispersed solids or other materials include any material known or otherwise suitable for topical application to human skin. The antiperspirant gel-solid stick compositions can also be formulated as gel-solid stick compositions that contain no antiperspirant or other active material, particulate or otherwise.

The gel-solid stick compositions can be prepared by methods well known in the formulation art for making gel-solids having minimal crystalline particle size or the preferred elongated particle morphology. The gel-solid stick compositions are preferably prepared by the select methods described hereinafter directed to minimizing crystalline particle size, or percentage, and/or establishing the preferred crystalline particle morphology.

Solid non-polymeric gellants suitable for use in the antiperspirant gel-solid stick compositions of the present invention include fatty acid gellants, esters and amides of fatty acid gellants, hydroxy acids, hydroxy fatty acids, cholesterolic materials, lanolinolic materials, and other amide gellants known for use as gelling agents or which are otherwise described in detail hereinafter. Other crystalline gellants can be used in the gel-solid stick compositions of the present invention provided that such other gellants can be formulated to provide the requisite crystalline gel matrix and product characteristics defined herein.

Other solid non-polymeric gellants suitable for use in the antiperspirant gel-solid stick compositions herein include fatty acid gellants which include, but are not limited to, fatty acid and hydroxy or alpha hydroxy fatty acids, having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred fatty acid gellants are those having the fatty acid dimer to monomer ratio as described hereinafter.

Suitable amide gellants include those specifically disclosed in U.S. Pat. No. 5,429,816 to Hofrichter. These solid non-polymeric gellants described herein are especially effective when used in combination with select anhydrous carriers such as volatile silicones, especially volatile cyclomethicone. These gellants are most preferably used in combination with a liquid carrier comprising a volatile silicone and a non-volatile silicone (e.g., non-volatile dimethicones or other organofunctional siloxanes well known in the art) and/or a non-volatile organic carrier.

The antiperspirant gel-solid stick compositions of the present invention may further comprise one or more optional components which may modify the physical, chemical or aesthetic characteristics of the compositions or serve as additional "active" components when deposited on the skin. The compositions may also comprise optional inert ingredients. Many such optional materials are known in the antiperspirant art and may be used in the antiperspirant compositions herein, provided that such optional materials are compatible with the essential materials described herein, or do not otherwise unduly impair product performance.

Non-limiting examples of optional materials include active components such as bacteriostats and fungiostats, insect repellants, UV absorbers, and "non-active" components such as pigments or colorants, moisturizing agents, protective agents, smoothing agents, antiseptic agents, sun-protecting agents, preservatives and/or antioxidants, perfumes, emulsifiers, chelants, distributing agents, residue masking agents, process aides such as viscosity modifiers, secondary structurants, cosmetic adjuncts, and wash-off aids. Examples of such optional materials are described in U.S. Pat. No. 4,049,792 to Elsnau; Canadian Patent 1,164,347 to Beckrneyer et al.; U.S. Pat. No. 5,019,375 to Tanner et al.; and U.S. Pat. No. 5,429,816 to Hofrichter et al.; all of which are incorporated herein by reference.

More specifically, such optional additives are more fully defined with the following non-limiting lists of potentially preferred compounds:

Pigments or coloring agents or combination of (opaque):
  Titanium dioxide
  Iron oxide
  Chromium oxide Chromic hydroxide
Ultramarine blue
Manganese violete
Mica-titanium dioxide pearls
Mica-iron oxides
Flourphogopite synthetic titanium dioxide
Moisturizing agents or combination of:
  glycerine
  hyaluronic acid
Protective agents or combination of:
  Ceramides
  Vitamin F
  Vitamins
Smoothing agents or combination of:
  Alpha bisabolol
  Chamomile extract
  escine
Antiseptic agents or combination of:
  Zeolites
  farnesol
Sun-protecting agents or combination of:
  Titanium dioxide
  zinc oxide
  octyl methoxycinamate
  Para-aminobenzoic acid
Preserving agents and antioxidants:
  Methyl paraben
  propyl paraben
  ascorbil palmitate
  alpha tocopherol
Microbiocides
Bactericides
Chlorinated aromatics
Triclosan
Chlorhexidine
Biguanide salts
Cosmosil™
Quaternary ammonium anticholinergics
glycopyrrolate
Wash-off Agents
  Non-ionic surfactants
    a. Esters/ethers (C8 to C22 polyoxyalkylene and/or polyol)
  Ionic surfactants
    b. sodium laureth Sulfate
Secondary structurants (non-polymeric or polymeric):
  Linear Fatty alcohol/wax
  Fatty acids ex. Stearic acid, sodium stearate, 12-hydroxy stearic acid
  Dibenzylidene alditols (DBS)
  N-acyl amino acid derivatives (N-Lauroyl glutamic acid dibutylamide,
  Amide derivatives of di or tribasic carboxylic acids: ex. N,N'-dialkylsuccinamides
  organo polysiloxane elastomers
  Polyamides
  Polymers containing both siloxane and hydrogen bonding groups
  polyacrylamides, polyacrylates, or polyakylene oxides (aqueous dispersed)
  Hydrogenated triglycerides ex. Hydrogenated castor oil
  Silica
  propylene carbonate
  Quaternium-18 bentonite or hectorite
  Alkyl silicone waxes, paraffin waxes, synthetic waxes
  Steroid derivatives—Lanosterol
  Starch/cellulosic Cosmetic adjuncts:
  Talc
  polyethylene (finely divided)
  Allantoin, lipids
  Colors
  Skin cooling agents ex. menthol
  perfume
  Sorbitol, Glycerine The antiperspirant gel-solid stick compositions of the present invention can also be formulated to comprise other dispersed solids or other materials in addition to or in place of the particulate antiperspirant active. Such other dispersed solids or other materials include any material known or otherwise suitable for topical application to human skin. The antiperspirant gel-solid stick compositions can also be formulated as gel-solid stick compositions which contain no antiperspirant or other active material, particulate or otherwise.

Method of Manufacture of Antiperspirant Sticks

The antiperspirant gel-solid stick compositions of the present invention may be prepared by any known or otherwise effective technique, suitable for providing an antiperspirant gel-solid stick composition having the requisite crystalline or amorphous matrix and other product characteristics described herein. Such methods involve formulation of the essential components of the composition to form a gel-solid having the requisite elastic to viscous moduli ratio, product hardness, and visible residue index. The crystalline matrix within the composition comprises elongated non-polymeric gellant crystals having an aspect ratio of greater than about 2, and preferably greater than about 6, and an average particle diameter that is minimized (in one aspect, to less than about 1 micron) through techniques directed to minimizing crystalline particle size in a composition.

Crystalline particle size in the preferred embodiments of the present invention can be determined by techniques well known in the art, which include light or electron microscopy study of the composition, wherein the composition is formulated for analysis purposes without particulate antiperspirant active or other solid particulates. Without such reformulation, it is more difficult to directly determine and distinguish crystalline gellant particle size and morphology from the particle size and morphology contributed from other non-gellant particulates. The reformulated composition is then evaluated by light or electron microscopy or other similar method.

Techniques for preparing the antiperspirant gel-solid stick compositions of the present invention include those methods suitable for formulating compositions containing small gellant crystalline particles. Suitable techniques for minimizing crystalline gellant particle size include the use of nucleating agents, formulation with select carriers or gellants or carrier/gellant combinations, controlling rates of crystallization including controlling formulation, controlling process flow rate, and processing temperatures, and other methods described herein. All such methods should be applied to the formulation to control or minimize gellant crystal particle size, and/or to form the desired elongated crystalline particles, to thus form the desired crystalline matrix of the composition.

The antiperspirant gel-solid stick compositions may be applied topically to the axilla or other area of the skin in an amount effective to treat or reduce perspiration wetness and malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and malodor control over an extended period.

Generally, it is necessary that the organic liquid used in cosmetic sticks is relatively non-toxic and compatible with the other ingredients comprising the cosmetic stick. For example, the cosmetic stick may contain one or more of antiperspirants (astringents), antibacterial agents, fragrances, surfactants, emulsifiers, emollients, colorants, fillers, moisturizers, etc., as is known in the art. In most cases, the organic liquid will be a solvent or carrier for the antiperspirant ingredient. Suitable organic liquids may be generally classified as aliphatic alcohols, polyhydric alcohols and polyethers. For example, the organic liquid may be selected from $C_2$-$C_6$ alcohols and polyethers of $C_1$-$C_4$ alkylenes, including ethanol, n-propanol, n-butanol, t-butanol, isopropanol, isobutanol, 2-methoxyethanol, 2-ethoxyethanol, ethylene glycol, propylene glycol, e.g. 1,2-propylene glycol, 1,3-propylene glycol, butylene glycol, e.g. 1,4-butylene glycol, 1,3-butylene glycol, 1,2-butylene glycol, 2,3-butylene glycol, diethylene glycol monomethylether, diethylene glycol monoethylether, 2,4-dihydroxy-2-methylpentane, glycerine, pentylene glycols and hexylene glycol; and polyethylene glycols (e.g., diethylene glycol), polypropylene glycols (e.g., dipropylene glycol, tripropylene glycol) and polypropylene polyethylene glycol copolymers.

In one aspect, the organic liquid is selected from $C_{2-6}$ dihydric alcohols such as ethylene glycol, 1,3-propylene glycol, 1,2-propylene glycol, 1,2-butylene glycol, 1,3-butylene glycol, 1,4-butylene glycol, 2,3-butylene glycol, 1,5-pentylene glycol and 1,6-hexylene glycol, and polyethylene glycols and polypropylene glycols having a molecular weight of 400 or less, such as diethylene glycol, dipropylene glycol and tripropylene glycol. Most preferably, the organic liquid is 1,2-propylene glycol. Those skilled in the art will recognize that the organic liquid may comprise mixtures of the aforementioned compounds and minor amounts of other miscible organic solvents, such as N-methyl-2-pyrrolidone or propylene carbonate, without deviating from the invention.

The organic liquid/bisurea gelator composition may be formed by mixing the components in a conventional stirring vessel. It will generally be most convenient to mix the components and store the composition at ambient temperature. Nevertheless, the composition may be mixed and stored in a chilled vessel, for example at temperatures down to 3° C. or lower. Heating the composition to too high a temperature (i.e., above 120° C., for instance) is likely to promote dissolution of the bisurea compound in the organic liquid, and gelation if the composition is cooled. Consequently, in one aspect, the composition is not heated above about 90° C.

The formulation of cosmetic sticks, including antiperspirant sticks, lipsticks, etc., with gelling agents is well known and may be found in the following references: WO-A-91/15191 to Oh et al.; CA-A-2,064,179 to Benfatto et al.; U.S. Pat. No. 4,722,835 to Schamper et al.; U.S. Pat. No. 4,725,430 to Schamper et al.; U.S. Pat. No. 4,781,917 to Luebbe et al.; U.S. Pat. No. 4,816,261 to Luebbe et al.; U.S. Pat. No. 5,200,174 to Gardlik et al.; U.S. Pat. No. 5,346,694 to Juneja; U.S. Pat. No. 5,376,363 to Benfatto et al.; U.S. Pat. No. 5,405,605 to Shin; U.S. Pat. No. 5,490,979 to Kasat et al.; and U.S. Pat. No. 5,609,855 to Oh et al.

According to the present invention, gels may be prepared by homogeneously admixing non-polar organic liquids with effectively small proportions of at least one non-polar solvent to form a gel (similar to that noted above fro the gelation of polar solvents). Basically, the gelling agents which may be employed in this invention can agglomerate to form a coherent structure and trap the non-polar organic liquid within the gel matrix.

Other Applications of Bisurea Gelling Agents

The gelling agent of the present invention is useful for the gelation of fuel oil and the recovery of drained oil. Furthermore, a wide variety of other materials can be prepared as for example, gelling or thixotropic agents for paints or inks, gelling agents for greases, solidifying agents for margarine comprising liquid oils, gelling agents or binders for liquid oil type cosmetics, binders or carriers for medicaments and gelling agents for napalm type incendiaries.

By the process of the present invention, gelled non-polar organic liquids are easily prepared with relatively simple procedures, and the inventive gelling agents are capable of gelling non-polar organic liquid using relatively small amounts of gelling agent.

In one aspect, the gelling agent of the present invention may be useful in cosmetic formulations. Cosmetic formulations may include at least one gelling agent of the present invention, at least one cosmetic solvent component, and at least one cosmetic active. Cosmetic solvent components include those solvents useful for preparing cosmetic formulations, such as, those taught in U.S. Pat. No. 5,505,937 to Castrogiovanni et al. As one non-limiting example, the gelling agent may be useful in lipstick formulations. Exemplary lipstick formulations includes those taught in U.S. Pat. No. 5,505,937 to Castrogiovanni et al.; U.S. Pat. No. 6,066,313 to Anton et al., and U.S. Pat. No. 6,908,621 to Jose et al. Herein, these patents teach cosmetic actives as including, without limitation, waxes, powders (dry, particulate matter), organic and inorganic pigments, volatile and non-volatile oils, preservatives, antioxidants, polymers, shine enhancers, vitamins, sunscreens, emulsifiers, biological additives, and the like, and mixtures thereof.

EXAMPLES

Having generally described the invention, a further understanding can be obtained by reference to certain specific examples which are provided herein for purposes of illustration only and are not intended to be limiting unless otherwise specified.

List of Reactants:

1. 1,6-diisocyanatohexane, (HDI) Desmodur H (Bayer)
2. 1,4-diisocyanatobutane (Aldrich)
3. 1,8-diisocyanatooctane (Aldrich)
4. 1,12-diisocyanatododecane (Aldrich)
5. (MDI) Desmodur M (Bayer)
6. (TMXDI) (Cytec)
7. (PPDI) (Aldrich)
8. 4,4'-Oxybis(phenyl isocyanate), (Aldrich)
9. Surfonamine® ML-300, renamed Surfonamine® B-30 (Huntsman)
10. PA-12 EH ether amine, (Tomah)
11. PA-14 ether amine, (Tomah)
12. PA-16 ether amine, (Tomah)
13. 3-(2-ethylhexyloxy)propylamine (TCl)

Synthesis of Bisurea Organic Gelling Agents

Example 1

Synthesis of Bisurea Gelling Agent 1 in Water

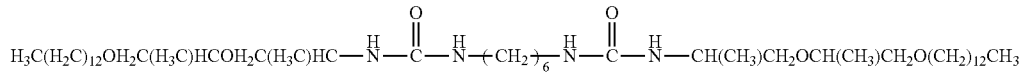

The drawn structure is an average representation of the product which is a mixture. The number of oxypropylene groups is a distribution with a mean equal to about 2 based on the average molecular weight of the amine; the terminal $C_{13}$ alkyl groups are a mixture of $C_{12}$ and $C_{14}$ alkyl groups.

4.2 g (25 mmol) of 1,6-diisocyantaohexane (HDI, Trade name Desmodur® H) from Bayer in the nitrogen protected addition funnel was slowly added into a mixture of 16 g (49 mmol) of Surfonamine® ML-300 from Huntsman and 250 mL water in a three-neck reaction flask equipped with temperature control and mechanical agitator. The temperature was controlled under 35° C. by cold water bath. After addition was completed, the reaction mixture was stirred at room temperature for 3 hours. The reaction mixture was filtered and the solid was washed with additional 250 mL of cold water. The solid product was dried overnight in a hood and 19.2 g of white granular product (yield 95%) was obtained.

Characterization:
$^1$H NMR (CDCl$_3$) was consistent with required structure.
FT-IR: 3328 cm$^{-1}$ (N—H), 1619 and 1574 cm$^{-1}$ (C=O).
Melting temperature: 84-92° C.

Example 2

Synthesis of Bisurea Gelling Agent 1 in Acetone 4.2 g of HDI (25 mmol) was added slowly into a mixture of 16 g of Surfonamine® ML-300 (49 mmol) and 150 mL of acetone under nitrogen at room temperature in a three-neck reaction flask equipped with temperature probe and mechanical agitator. White precipitate was formed in the flask. After addition was completed, the reaction mixture was stirred for three hour and monitored with FTIR to make sure all NCO groups were reacted. The suspension was filtered and the solid was washed with 100 mL of acetone. 14.5 g of white powder product (yield 72%) was obtained after drying.

Characterization:
$^1$H NMR (CDCl$_3$) was consistent with required structure.
FT-IR: 3329 cm$^{-1}$ (N—H), 1618 and 1570 cm$^{-1}$ (C=O).
Melting temperature: 84-95° C.

Example 3

Synthesis of Bisurea Gelling Agent 1 in Toluene 33.6 g of HDI (0.2 mol) was added slowly into a mixture of 128 g of Surfonamine® ML 300 (0.4 mol) and 500 mL of toluene at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was poured into 1000 mL of acetone and the precipitate was filtered, washed with 500 mL of acetone and dried. The product was white, wax-like solid (yield: 128 g, 79.5%).

Characterization:
$^1$H NMR (CDCl$_3$) was consistent with required structure.
FT-IR: 3328 cm$^{-1}$ (N—H), 1619 and 1568 cm$^{-1}$ (C=O).
Melting temperature: 84-94° C.

Example 4

Synthesis of Bisurea Gelling Agent 2 in Acetone

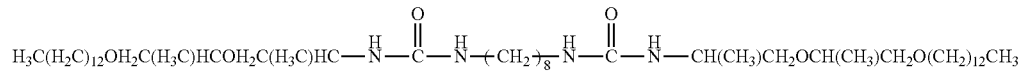

The above compound was synthesized (92% yield) following the similar procedure of Example through the reaction of 1,4-diisocyanatobutane and Surfonamine® ML-300.

Characterization:
$^1$H NMR (CDCl$_3$) was consistent with required structure.
FT-IR: 3332 cm$^{-1}$ (N—H), 1620 and 1571 cm$^{-1}$ (C=O).
Melting temperature: 109-116° C.

Example 5

Synthesis of Bisurea Gelling Agent 3 in Acetone

The above compound was synthesized (83% yield) following the similar procedure of Example 3.

Characterization:
$^1$H NMR (CDCl$_3$) was consistent with required structure.
FT-IR: 3327 cm$^{-1}$ (N—H), 1619 and 1570 cm$^{-1}$ (C=O).
Melting temperature: 85-91° C.

Example 6

Synthesis of Bisurea Gelling Agent 4 in Acetone

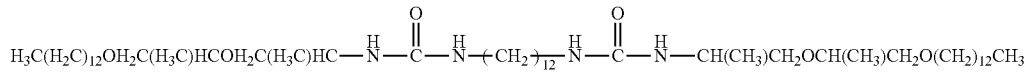

The above compound was synthesized (91% yield) following the similar procedure of Example 1.

Characterization:
$^1$H NMR (CDCl$_3$) was consistent with required structure.
FT-IR: 3337 cm$^{-1}$ (N—H), 1617 and 1571 cm$^{-1}$ (C=O).
Melting temperature: 79-86° C.

Example 7

Synthesis of Bisurea Gelling Agent 5 in Toluene

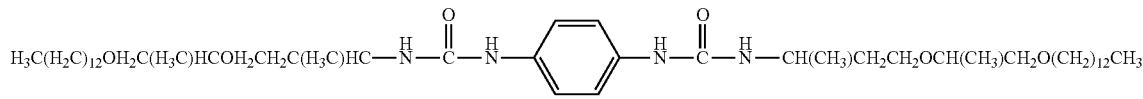

A mixture of 32.5 g of Surfonamine® ML-300 (100 mmol) and 100 mL of toluene was added slowly into a solution of 8.0 g of para-phenylene diisocyanate (50 mmol, PPDI from Dupont, trade name Hylene® PPDI) in 100 mL of toluene in a three-neck reaction flask equipped with temperature probe and mechanical agitator under nitrogen blanket at room temperature. After addition was completed, the reaction mixture was held for one hour and a sample was taken for FTIR analysis to confirm that NCO groups were reacted. The mixture was filtered and the solid was washed with 200 mL of acetone. After drying, 22.7 g of white powder product (56% yield) was obtained.

Characterization:
$^1$H NMR (CDCl$_3$) was consistent with required structure.
FT-IR: 3305 cm$^{-1}$ (N—H), 1629 and 1568 cm$^{-1}$ (C=O).
Melting temperature: 175-185° C.

Example 8

Synthesis of Bisurea Gelling Agent 6 in Toluene

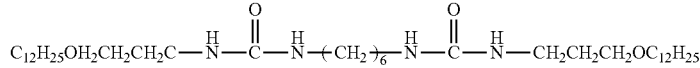

3.4 g of HDI (0.02 mol) was added slowly into a mixture of 10.1 g of Ether amine PA-16 from Tomah Product, Inc. (0.04 mol) and 50 mL of toluene at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was poured into 100 mL of acetone and the precipitate was filtered, washed with 50 mL of acetone and dried. The product was white, wax-like solid (yield 71.5%).

Characterization:
$^1$H NMR (CDCl$_3$) was consistent with required structure.
FT-IR: 3328 cm$^{-1}$ (N—H), 1616 and 1577 cm$^{-1}$ (C=O).
Melting temperature: 155-170° C.

Example 9

Synthesis of Bisurea Gelling Agent 7 in Cyclohexane

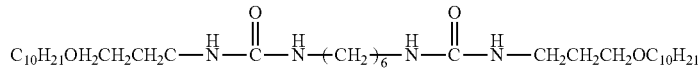

6.72 g of HDI from Aldrich (0.04 mol) was added slowly into a mixture of 18.0 g of Ether amine PA-14 from Tomah Product, Inc. (0.08 mol) and 200 mL of cyclohexane at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was poured into 400 mL of acetone and the precipitate was filtered, washed with 100 mL of acetone and dried. The product was white, wax-like solid (yield: 18.5 g, 75%).

Characterization:
$^1$H NMR (CDCl$_3$) was consistent with required structure.
FT-IR: 3324 cm$^{-1}$ (N—H), 1616 and 1573 cm$^{-1}$ (C=O).
Melting temperature: 135-142° C.

Example 10

Synthesis of Bisurea Gelling Agent 8 in Toluene

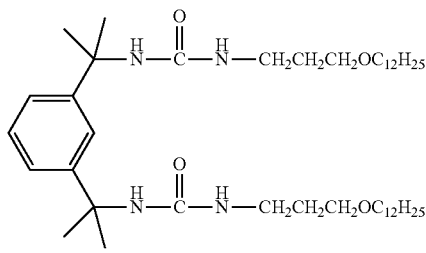

4.9 g of TMXDI from Cytec (0.02 mol) was added slowly into a mixture of 10.1 g of Ether amine PA-16 from Tomah

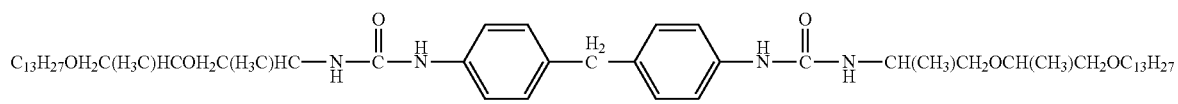

Product, Inc. (0.04 mol) and 100 mL of toluene at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was poured into 400 mL of acetone and the precipitate was filtered, washed with 100 mL of acetone and dried. The product was white, wax-like solid (yield 72%).

Characterization:
$^1$H NMR (CDCl$_3$) was consistent with required structure.
FT-IR: 3328 cm$^{-1}$ (N—H), 1631 and 1562 cm$^{-1}$ (C═O).
Melting temperature: 152-157° C.

Example 11

Synthesis of Bisurea Gelling Agent 9 in Cyclohexane

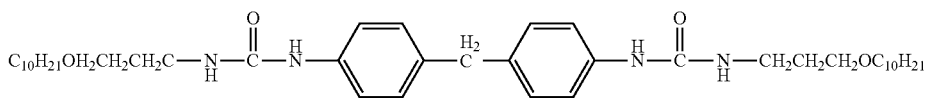

6.25 g of Desmodur ML (MDI) from Bayer (0.025 mol) was added slowly into a mixture of 11.3 g of Ether amine PA-14 from Tomah Product, Inc. (0.05 mol) and 100 mL of cyclohexane at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was poured into 400 mL of acetone and the precipitate was filtered, washed with 100 mL of acetone and dried. The product was white, wax-like solid (yield: 78%).

Characterization:
$^1$H NMR (CDCl$_3$) was consistent with required structure.
FT-IR: 3305 cm$^{-1}$ (N—H), 1631 and 1565 cm$^{-1}$ (C═O).
Melting temperature: 180-190° C.

Example 12

Synthesis of Bisurea Gelling Agent 10 in Toluene 32.0 g of Surfonamine® ML-300 from Huntsman (0.10 mol) was added slowly into a mixture of 12.5 g of MDI from Aldrich (0.05 mol) and 200 mL of toluene at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was poured into 400 mL of acetone and the precipitate was filtered, washed with 100 mL of acetone and dried. The product was white, wax-like solid (yield: 79.5%).

Characterization:
$^1$H NMR (CDCl$_3$) was consistent with required structure.
FT-IR: 3305 cm$^{-1}$ (N—H), 1631 and 1558 cm$^{-1}$ (C═O).
Melting temperature: 134-141° C.

Example 13

Synthesis of Bisurea Gelling Agent 11 with Mixed Amines 8.4 g of HDI from Bayer (0.05 mol) was added slowly into a mixture of 16.6 g of Surfonamine® ML-300 from Huntsman (0.051 mol), 6.6 g 2-ethylhexylamine (0.051 mol) and 200 mL of acetone at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was filtered, washed with 100 mL of acetone and dried. The product was white solid (yield: 50%).

Characterization:
FT-IR: 3328 cm$^{-1}$ (N—H), 1619 and 1569 cm$^{-1}$ (C=O).
Melting temperature: 70-80° C.

Example 14

Synthesis of Bisurea Gelling Agent 12 with Mixed Amines 8.4 g of HDI from Bayer (0.05 mol) was added slowly into a mixture of 16.6 g of Surfonamine® ML-300 from Huntsman (0.051 mol), 10.6 g PA-12 EH from Tomah (0.051 mol) and 250 mL of acetone at room temperature under nitrogen blanket in a three-neck reaction flask equipped with temperature controller and mechanical agitator. After addition was completed, the reaction mixture was stirred at room temperature for three hours. The reaction was monitored with FTIR until no more NCO functional group presented. The mixture was filtered, washed with 100 mL of acetone and dried. The product was white solid (yield: 69.7%).

Characterization:
FT-IR: 3328 cm$^{-1}$ (N—H), 1619 and 1573 cm$^{-1}$ (C=O).
Melting temperature: 105-110° C.

Organic Gels

Example 15A

Organic Gels Formed by Gelling Agent 1

The organic gels were prepared by adding certain amount of gelling agent 1 into the organic liquid in a test tube, then heat the mixture to higher temperature until the gelling agent is completely dissolved, and then cool the mixture to room temperature. The dissolution temperature is the temperature when the mixture is completely clear. The presence or absence of a clear gel with various solvents is shown in Table 1. A clear gel is a transparent gel. Clear stable gels were made with aprotic, non-polar solvents with a dielectric constant that is less or equal than ~4.5 reported at 20-25° C., except for the tribromomethane solvent which has a dielectric constant equal to 4.4 and did not gel. Solvents with a dielectric constant of less 15 are considered to be non-polar. An aprotic solvent is a solvent that has no hydrogen atom bound to an oxygen as in a hydroxyl group nor a nitrogen as in an amine group.

TABLE 1

Various Organic Gels of Gelling Agent 1[a]

| Sample Number | Solvents or mixture | Dissolution temp. (° C.) | Gel Appearance | Dielectric Constant | Aprotic Solvent |
|---|---|---|---|---|---|
| 1 | n-Dodecane[c] | 97 | Clear stable gel | 2.0 | Yes |
| 2 | Mineral oil | 97 | Clear stable gel | 2.1 | Yes |
| 3 | Hydrogenated polydecene | 100 | Clear stable gel | 2.1 | Yes |
| 4 | Hydrogenated polyisobutene | 100 | Clear stable gel | — | Yes |
| 5 | PPG-14 butyl ether | 92 | Clear stable gel | — | Yes |
| 6 | POE-40 castor oil | 96 | Slight haze gel | — | Yes |
| 7 | Toluene[c] | 76 | Clear stable gel | 2.4 | Yes |
| 8 | Linoleic Acid[c] | 80 | No gel | 2.7 | No |
| 9 | Butyl Stearate[c] | 88 | Slight haze gel | 3.1 | Yes |
| 10 | Isopropyl palmitate | 93 | Clear stable gel | 3.2 | Yes |
| 11 | Isopropyl myristate | 93 | Clear stable gel | 3.2 | Yes |
| 12 | Dibenzylamine[c] | 93 | Opaque stable gel | 3.6 | No |
| 13 | C12-15 Alkyl benzoate | 93 | Clear stable gel | 3.8 | Yes |
| 14 | Butyl Oleate[c] | 94 | Clear stable gel | 4.0 | Yes |
| 15 | Tribromomethane[c] | 41 | No gel | 4.4 | Yes |
| 16 | PPG-3 Benzyl ether myristate[b] | 90 | Clear stable gel | 4.5 | Yes |
| 17 | diiodobenzene[c] | 150 | No gel | 4.6 | Yes |
| 18 | Chloroform[c] | 35 | No gel | 4.7 | Yes |
| 19 | Ethyl acetate[c] | 76 | Partial gel | 6.0 | Yes |
| 20 | Methylene Chloride[c] | 31 | No gel | 9.1 | Yes |
| 21 | 1-Octanol[c] | 79 | No gel | 10.0 | No |
| 22 | Benzyl Alcohol[c] | 86 | No gel | 13.1 | No |

[a]Gelling agent usage is 1% wt. unless specified otherwise
[b]Crodamol ® STS from Croda Inc.
[c]2% wt. gelling agent 1 in the solvents.

Both of the bisurea gelling agents from this invention and the gels made from bisurea gelling agents were immersed in the pH buffers from pH=2 to pH=12 at room temperature for one month. There were no observable changes on the composition of both gelling agents and the gels based on GC/MS analysis. So, the bisurea gelling agents and the organic gels of the present invention are stable in pH=2 to pH=12 buffers at room temperature for long periods of time.

Example 15B

Gel of Mineral Oil by Gelling Agent 13

The organic gel was prepared by adding 2% by weight of gelling agent 13 into the light mineral oil in a jar, then heat the mixture to higher temperature while mixing with a magnetic stir bar until the gelling agent is completely dissolved. Then the mixture was cooled to room temperature. A clear gel was produced. The dissolution temperature was about 100° C.

Cosmetic Compositions

Example 16

Antiperspirant and Deodorant Sticks

A number of antiperspirant and deodorant sticks were prepared as the following method. The liquids, waxes and gelling agents were first mixed together in a glass flask and heated until a uniform clear solution is formed. Once the gelling agents and waxes were melted or dissolved, the antiperspirant actives and talc were added and the whole mixture was cooled to about 10° C. above the gelling temperature. Then, fragrance was added. The mixture was stirred for several minutes and poured into stick containers and cooled at room temperature. Thermal stability, hardness and white residue measurements were performed as described earlier after the sticks had been aged at room temperature overnight to evaluate their properties.

| Ingredients | Parts by weight | | |
|---|---|---|---|
| | Example 16A | Example 16B | Example 16C |
| DC-245 fluid | 35.8 | 48.8 | 28.3 |
| Finsolv TN | 20.0 | 15.0 | |
| Panatane L 14$^E$ | | | 16.0 |
| Demethicone 100 cst | | | 2.0 |
| Stearyl alcohol | | | 14.0 |
| Hydrogenated castor oil | 10.0 | | 2.5 |
| Glyceryl monostearate | | | 2.5 |
| Behenyl Erucate | | | 3.0 |
| Uniline 350 | | | 2.5 |
| Uniline 700 | 5.0 | 10.0 | |
| Gelling Agent 1 from this invention | 2.0 | 2.0 | 2.0 |
| Talc | 3.0 | | 3.0 |
| Fragrance | 0.2 | 0.2 | 0.2 |
| AZP 908 powder | 24.0 | 24.0 | 24.0 |
| Total | 100.0 | 100.0 | 100.0 |
| Thermal stability (45° C.) | pass | pass | pass |
| Hardness (g force) | 595 | 504 | 366 |
| White residue on fabric, ΔL | 4.94 | 5.60 | 7.39 |

These antiperspirant formulations showed very good thermal storage stability and appropriate hardness for applying on skin. The white residue on fabric is less than that of antiperspirant formulations without the gelling agent 1 from this invention.

Example 17

Antiperspirant and Deodorant Soft-Solids/Creams

A series of antiperspirant creams (or soft solids) were prepared as following: Liquids, waxes and gelling agents were mixed in a flask and heated to above the dissolution temperature and a clear, uniform liquid solution was formed. Talc or/and silica and antiperspirant actives were added and the mixture was mixed, poured into cream containers and cooled to room temperature. The formulations' stability was assessed at both room temperature and elevated temperature (45° C. oven) for one month. The formulations will be rated pass if no clear phase separation, color change, or syneresis is observed.

| Ingredients | Parts by weight | | |
|---|---|---|---|
| | Example 17A | Example 17B | Example 17C |
| DC-245 fluid | 46.1 | 58.75 | 51.0 |
| Finsolv TN | 9.0 | | 15.0 |
| Panatane L 14$^E$ | 9.0 | 10.0 | |
| Hydrogenated castor oil | 2.6 | | |
| Syncrowax HGL-C | | 1.25 | |
| Syncrowax HRC | | 5.0 | |
| Rheopearl KL | | | 2.0 |
| Gelling Agent 1 from this invention | 1.0 | 1.0 | 2.0 |
| Talc | 6.0 | | 6.0 |
| Cab-O-Sil M5 | 4.3 | | |
| AZP 908 powder | 24.0 | 24.0 | 24.0 |
| Total | 100.0 | 100.0 | 100.0 |
| Thermal stability | pass | pass | pass |

Example 18

Lipstick Formulation

| | Lipstick Formulation |
|---|---|
| Ingredients | Parts by weight Example 18 |
| Castor oil | 42 |
| AMS-C30 Cosmetic wax | 20 |
| Gelling Agent 1 from this invention | 2 |
| DC 245 | 20 |
| TiO2 | 6 |
| Mica | 10 |
| Total | 100.0 |
| Thermal stability | pass |

Example 19

Sunscreen Gels

| Ingredients | Parts by weight | | |
|---|---|---|---|
| | Example 19A | Example 19B | Example 19C |
| DC-245 fluid | 40.0 | 62.5 | 60.0 |
| Finsolv TN | 42.0 | 20.0 | 20.0 |
| Microcrystalline wax | 1.0 | | |
| Dow Corning AMS C30 wax | 5.0 | 4.0 | 4.0 |
| Syncrowax HR-C | | 2.0 | 2.0 |
| Gelling Agent 1 from this invention | 1.0 | 1.0 | 1.0 |
| Parsol 1789 | | 3.0 | 3.0 |
| ZnO paste | | | 10.0 |
| Octyl methoxycinnamate | 8.0 | 7.5 | |
| Benzophenone-3 | 3.0 | | |
| Fragrance | 0.2 | 0.2 | 0.2 |
| Total | 100.0 | 100.0 | 100.0 |

Water-free oil gels are soft and water resistant. Silicones in formulation improve the non-greasy and non-sticky feeling. The example sunscreen formulations were uniform and stable at room temperature.

Example 20

Clear Candle Gel

| Ingredients | Part in weight % |
|---|---|
| Mineral oil | 98.0 |
| Gelling Agent 1 from this invention | 2.0 |
| Total | 100 |

The gel was prepared by heating the mixture of mineral oil and gelling agent 1 to completely clear, adding wick inside, and then was cooled at room temperature. The gel was transparent and stable in room temperature for at least 6 months. It was burned with stable flame.

Example 21

Slow Release of Fragrances with Fragrance Gels

The bisurea organic gels were made as in Example 15 for mixed organic solvents. The evaporation rates of both the solvent mixture and the correspondent gel were compared as mass loss percentage along the time at ambient condition.

| Sample ID | Formulation (wt. %) | % Loss 18 h | % Loss 42 h | % Loss 66 h | % Loss 90 h |
|---|---|---|---|---|---|
| Ex. 21 a | Ethyl acetate/Finsolv TN (70/30) | 33.1 | 61.3 | 70.7 | 70.8 |
| Ex. 21 b | 2% Gelling Agent 1 98% mixture of Ethyl acetate/Finsolv TN (70/30) | 39.5 | 57.1 | 62.6 | 68.0 |
| Ex. 21 c | Butyl acetate/Finsolv TN (70/30) | 10.7 | 26.5 | 40.7 | 65.4 |
| Ex. 21 d | 2% Gelling Agent 1 98% mixture of Butyl acetate/Finsolv TN (70/30) | 8.4 | 21.6 | 31.5 | 55.2 |

From these experiments, it is clear that the organic gels have slower evaporation rate compared with the corresponding organic solvents. Small percentage of gelling agents of the present invention can slow the release of volatile organic compounds.

Example 22

Water-Resistance of the Gel Formulations Made from the Bisurea Gelling Agents of the Present Invention

| | Parts by weight | |
|---|---|---|
| Ingredients | Ex. 22a | Ex. 22b |
| Finsolve TN | 25.0 | 25.0 |
| Mineral Oil | 60.0 | 58.0 |
| TiO$_2$ pigment | 15.0 | 15.0 |
| Gelling Agent 1 | — | 2.0 |
| Total | 100.0% | 100.0% |

Formulation of Example 22a was prepared by mixing the three components together. Example 22b was prepared by heating Finsolve TN, Mineral oil and gelling agent 1 to completely dissolve, then adding TiO$_2$ pigment to mix, cooling to room temperature. Both Ex. 22a and 22b were applied on leather, then allow half hour under ambient condition to dry. Then the two leather sample with Ex. 22a and Ex. 22b were immersed in water. The white pigment on leather with Ex. 22a was washed off immediately, while the TiO$_2$ pigment on the leather with Ex. 22b stay on the leather even after a day in the water. This experiment shows that gelled pigment preparations are water resistant and stick to the surface better.

Example 23

Synthesis of Bisurea Gelling Agent 1 in Acetone with Water Addition 43.2 g of HDI (257 mmol) was added slowly over a period 47 minutes into a mixture of 160 g of Surfonamine® B-30 (492 mmol) and 500 mL of acetone under nitrogen at room temperature in a three-neck reaction flask equipped with temperature probe and mechanical agitator. Temperature increased to 29.7° C. during the addition of HDI due to the reaction exotherm, and decreased back to room temperature over the course of the reaction. White precipitate was formed in the flask. After addition was completed, the reaction mixture was stirred for 5.5 hours and monitored with FTIR to make sure all NCO groups were reacted. A volume of 500 ml of water was added to the reactor. The suspension was filtered on a Buchner funnel and the solids were washed further with 1.0 L of water poured over the filter cake. The recovered solids were slurred into 1.0 L of water. The slurry was filtered again and the solids were washed further with 1.0 L of water poured over the filter cake. The washing procedure was repeated one more time. About 177 g of white powder product (yield 87%) was obtained after drying.

Characterization:

$^1$H NMR (CDCl$_3$) was consistent with required structure. FT-IR: 3329 cm$^{-1}$ (N—H), 1618 and 1570 cm$^{-1}$ (C=O).

Melting temperature measured by electrothermal method (using 2 C/min ramp rate): onset at 94.3° C. and full melt at 105.6° C.

Example 24

Synthesis of Bisurea Gelling Agent 1 in Acetone with Methanol Addition 43.2 g of HDI (257 mmol) was added slowly over a period 36 minutes into a mixture of 160 g of Surfonamine® B-30 (492 mmol) and 500 mL of acetone under nitrogen at room temperature in a three-neck reaction flask equipped with temperature probe and mechanical agitator. Temperature increased to 32.3° C. during the addition of HDI due to the reaction exotherm, and decreased back to room temperature over the course of the reaction. White precipitate was formed in the flask. After addition was completed, the reaction mixture was stirred for 5.5 hours and monitored with FTIR to make sure all NCO groups were reacted. A volume of 500 ml of methanol was added to the reactor. The suspension was filtered on a Buchner funnel and the solids were washed further with 1.0 L of water poured over the filter cake. The recovered solids were slurred into 1.0 L of water. The slurry was filtered again and the solids were washed further with 1.0 L of water poured over the filter cake. The washing procedure was repeated one more time. About 81.4 g of white powder product (yield 40%) was obtained after drying.

Characterization:

$^1$H NMR (CDCl$_3$) was consistent with required structure. FT-IR: 3329 cm$^{-1}$ (N—H), 1618 and 1570 cm$^{-1}$ (C=O).

Melting temperature measured by electrothermal method (using 2 C/min ramp rate): onset at 95.1° C. and full melt at 105.9° C.

Example 25

Synthesis of Gelling Agent 13 in Methanol 100 g of HDI (0.6 mol) was added slowly over a period 26 minutes into a mixture of 370 g of Surfonamine® B-30 (1.14 mol) and 400 mL of methanol under nitrogen at room temperature in a three-neck reaction flask equipped with temperature probe and mechanical agitator. Temperature increased to 30.6° C. during the addition of HDI due to the reaction exotherm, and decreased back to room temperature over the course of the reaction. White precipitate was formed in the flask. After addition was completed, the reaction mixture was stirred for two and an half hours and monitored with FTIR to make sure all NCO groups were reacted. A volume of 1 L of de-ionized water was added to the reactor. The suspension was filtered on a Buchner funnel. The solids were washed further with 3 L of water poured over the filter cake. The solids were air dried overnight. About 458.9 g of white powder product (yield 97.6%) was obtained.

The solids were washed further; they were added to 1.0 L of de-ionized water and slurried. The slurry was filtered and the solids were washed further with 1.0 L of water poured over the filter cake. The washing procedure was repeated one time. The solids were air dried overnight.

Characterization:

$^1$H NMR (CDCl$_3$) shows that the product is a mixture of Gelling Agent 1 and the following mono-urea/mono-urethane compound formed by reaction of HDI with one Surfonamine and one methanol solvent molecule, as shown below.

TABLE A

Visual Evaluation of Clarity

| Number | Description | Property |
|--------|-------------|----------|
| 5 | Clear | Transparent |
| 4 | Semi-Clear | Easily Read |
| 3 | Translucent | Fuzzy |
| 2 | Hazy | Barely Discernible |
| 1 | Cloudy | Unable to See Markings |

Similar test methods for clarity are disclosed in U.S. Pat. No. 2,967,178 to Kerr et al. and U.S. Pat. No. 5,451,396 to Villars.

A combination of the above-described methods was used to evaluate gel clarity for the gelling agent of the present invention. Light mineral oil was used as the solvent and reference point for 100% light transmission. Test results are provided in Table 2.

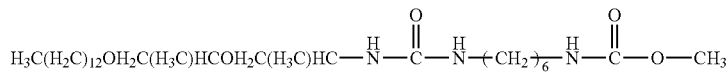

The drawn structure is an average representation of the mono-urea/mono-urethane compound which is a mixture. The number of oxypropylene groups is a distribution with a mean equal to 2; the terminal C13 alkyl groups are a mixture of C12 and C14 alkyl groups.

The hydrogen atoms of the terminal methoxy group give rise to a singlet peak at ~3.65-3.66 ppm in the $^1$H NMR spectrum of gelling agent 13 as compared to the NMR spectrum of gelling agent 1.

The molar percent concentration of the mono-urea/mono-urethane compound in gelling agent 13 is about 24-31% based on the peak area of the singlet of the methoxy group and the singlet of the terminal methyl group at ~0.88 ppm.

LC-MS: The mono-urea/mono-urethane compound gives rise to additional peaks in the LC-MS that are consistent with the structure.

FT-IR: 3329 cm$^{-1}$ (N—H), 1618 and 1570 cm$^{-1}$ (C=O).

Melting temperature measured by electrothermal method (using 2 C/min ramp rate): onset at 80.5° C. and full melt at 92.8° C.

Example 26

According to one embodiment of the present invention, gel clarity may be measured, at 25° C., as the percent light transmission on an aqueous paste at a particular wavelength (such as λ=640 nm) using a spectrophotometer, with water or light mineral oil as reference at 100 percent.

In addition, gel clarity may be determined by filling a disposable 3.0 cc syringe with the gelling agent or gelled solvent system and by visually assigning a clarity number which correlates to the appearance of the markings on the syringe as described in Table A.

TABLE 2

Clarity of Gelling Agent

| Concentration of Gelling Agent 1 | Visual Observation | % Transmitted Light at 640 nm |
|---|---|---|
| 2 | Clear | 94.7 |
| 5 | Clear | 97.4 |
| 10 | Clear | 97.8 |
| 16 | Semi-Clear | 77.2 |

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A gelled solvent system comprising at least one gelling agent represented by the structure of Formula (I)

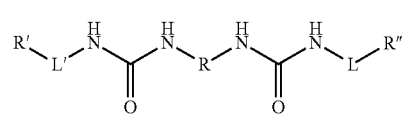

wherein R is a C$_3$-C$_{18}$ linear, branched, or cyclic moiety; and R' and R" may be the same or different and are selected from the group consisting of C$_1$-C$_{36}$ linear or branched alkanes or aryl alkanes, α-methyl branched C$_2$-C$_{36}$ alkanes, α-methyl branched C$_2$-C$_{36}$ ethers, β-methyl branched C$_2$-C$_{36}$ alkanes, and β-methyl branched C$_2$-C$_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units;

wherein the system is a pourable liquid above the dissolution temperature and the system is a stable gel below the gelling temperature;

wherein the system is pH stable in the range from pH=2 to pH=12; and wherein the system is water resistant and has superior adhesion properties.

2. The gelled solvent system of claim 1, wherein said system comprises at least about 1% of a wax component by weight and at least about 0.1% to about 20% by weight of said at least one gelling agent.

3. The gelled solvent system of claim 1, wherein when said system comprises a fragrance, and wherein the fragrance evaporation rate is lower than that of a solvent system without the gelling agent.

4. The gelled solvent system of claim 1, wherein the at least one gelling agent exhibits a gel temperature of at least 20° C. and a dissolution temperature of at most 200° C. in a non-polar solvent.

5. The gelled solvent system of claim 1, wherein said system includes at least one non-polar solvent.

6. The gelled solvent system of claim 5, wherein the non-polar solvent has a dielectric constant of less than or equal to 15.0.

7. The gelled solvent system of claim 5, wherein the non-polar solvent has a dielectric constant of less than or equal to 10.0.

8. The gelled solvent system of claim 5, wherein the non-polar solvent has a dielectric constant of less than or equal to 5.0.

9. The gelled solvent system of claim 5, wherein the non-polar solvent has a dielectric constant of less than or equal to 4.0.

10. The gelled solvent system of claim 5, wherein the non-polar solvent is an aprotic solvent.

11. The gelled solvent system of claim 1, wherein the gelled solvent system is clear.

12. The gelled solvent system of claim 1, wherein the gelled solvent system contains between about 0.001% and about 20.0% of the at least one gelling agent.

13. The gelled solvent system of claim 1, wherein the gelled solvent system contains between about 0.001% and about 15.0% of the at least one gelling agent.

14. The gelled solvent system of claim 1, wherein the gelled solvent system contains between about 0.001% and about 10.0% of the at least one gelling agent.

15. The gelled solvent system of claim 1, wherein the gelled solvent system contains between about 0.001% and about 5.0% of the at least one gelling agent.

16. The gelled solvent system of claim 1, wherein the gelled solvent system contains between about 0.001% and about 4.0% of the at least one gelling agent.

17. An antiperspirant gel formulation comprising:
(i) at least one gelling represented by the structure of Formula (I)

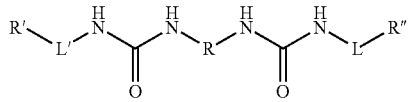

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units;

(ii) at least one antiperspirant solvent component, and (iii) at least one antiperspirant active;

wherein the gel formulation is a pourable liquid above the dissolution temperature and the system is a stable gel below the gelling temperature;

wherein the gel formulation is pH stable in the range from pH=2 to pH=12; and wherein the gel formulation is water resistant and has superior adhesion properties.

18. The antiperspirant gel formulation of claim 17, wherein the formulation is clear.

19. A cosmetic gel formulation comprising at least one gelling agent represented by the structure of Formula (I), at least one cosmetic solvent component, and at least one cosmetic active.

20. The cosmetic gel formulation of claim 19, wherein the formulation is clear.

21. A candle gel formulation comprising:
(i) at least one gelling represented by the structure of Formula (I)

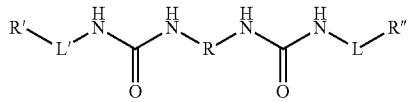

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units; and

43

(ii) at least one candle solvent component;
wherein the gel formulation is a pourable liquid above the dissolution temperature and the system is a stable gel below the gelling temperature;
wherein the gel formulation is pH stable in the range from pH=2 to pH=12; and
wherein the gel formulation is water resistant and has superior adhesion properties.

22. The candle gel formulation of claim 21, wherein the formulation is clear.

23. A gelled solvent system comprising at least one gelling agent represented by the structure of Formula (I)

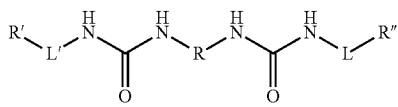

wherein R is a $C_3$-$C_{18}$ linear or branched alkylene chain or an aromatic ring; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;
wherein if R' and R" are the same, then both of said groups is selected from the group consisting of α-methyl branched $C_2$-$C_{18}$ ethers and β-methyl branched $C_2$-$C_{18}$ ethers;
wherein L and L' may be same or different and are selected from the group consisting of ethylene oxide chains, propylene oxide chains, and mixtures thereof, and the chains may comprise one or a plurality of repeat units;
wherein the system is a pourable liquid above the dissolution temperature and the system is a stable gel below the gelling temperature;
wherein the system is pH stable in the range from pH=2 to pH=12; and
wherein the system is water resistant and has superior adhesion properties.

24. The gelled solvent system of claim 23, wherein the at least one gelling agent exhibits a gel temperature of at least 20° C. and a dissolution temperature of at most 200° C. in a non-polar solvent.

25. The gelled solvent system of claim 23, wherein said system includes at least one non-polar solvent.

26. A gelled solvent system comprising at least one gelling agent represented by the structure of Formula (I)

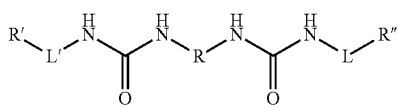

wherein R is a $C_3$-$C_{18}$ linear, branched or cyclic moiety selected from the group consisting of unsubstituted or substituted phenyl, phenyl ether, and phenyl methylene; and R' and R" may be the same or different and are selected from the group consisting of $C_1$-$C_{36}$ linear or branched alkanes, α-methyl branched $C_2$-$C_{36}$ alkanes or aryl alkanes, α-methyl branched $C_2$-$C_{36}$ ethers, β-methyl branched $C_2$-$C_{36}$ alkanes, and β-methyl branched $C_2$-$C_{36}$ ethers;

44 wherein if R' and R" are the same, then both of said groups is selected from the group consisting of α-methyl branched $C_2$-$C_{18}$ ethers and β-methyl branched $C_2$-$C_{18}$ ethers;
wherein L and L' may be same or different and are selected from the group consisting of ethylene oxide chains, propylene oxide chains, and mixtures thereof, and the chains may comprise one or a plurality of repeat units;
wherein the system is a pourable liquid above the dissolution temperature and the system is a stable gel below the gelling temperature;
wherein the system is pH stable in the range from pH=2 to pH=12; and
wherein the system is water resistant and has superior adhesion properties.

27. The gelled solvent system of claim 26, wherein the at least one gelling agent exhibits a gel temperature of at least 20° C. and a dissolution temperature of at most 200° C. in a non-polar solvent.

28. The gelled solvent system of claim 26, wherein said system includes at least one non-polar solvent.

29. A gelled solvent system comprising a mixture of at least one gelling agent represented by the structure of Formula (I),

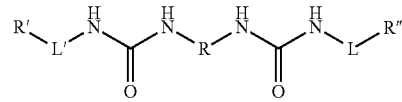

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;
wherein if R' and R" and the same, then both of said groups is selected from the group consisting of α-methyl branched $C_2$-$C_{18}$ ethers and β-methyl branched $C_2$-$C_{18}$ ethers;
wherein L and L' may be same or different and are selected from the group consisting of ethylene oxide chains, propylene oxide chains, and mixtures thereof, and the chains may comprise one or a plurality of repeat units, and one compound represented by the structure of Formula (II) or Formula (III),

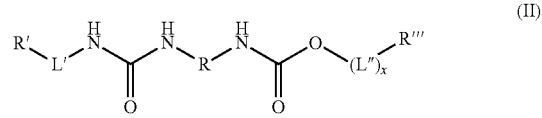

wherein R is a $C_3$-$C_{18}$ linear, branched, or cyclic moiety; and R' is selected from the group consisting of $C_2$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;
wherein L' is selected from the group consisting of ethylene oxide chains, propylene oxide chains, and mixtures thereof, and the chains may comprise one or a plurality of repeat units;
wherein R'" is selected from the group consisting of H, $CH_3$, $C_2$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein x=0 or 1 and L" is selected from the group consisting of ethylene oxide chains, propylene oxide chains, and mixtures thereof, and the chains may comprise one or a plurality of repeat units, $$R'-(L')_y-O-C(=O)-NH-R-NH-C(=O)-O-(L'')_x-R''' \qquad (III)$$

wherein R is a $C_3$-$C_{18}$ linear, branched, or cyclic moiety, and R' and R''' are selected from the group consisting of H, $CH_3$, $C_2$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein x=0 or 1 and y=0 or 1 and, L' and L" are selected from the group consisting of ethylene oxide chains, propylene oxide chains, and mixtures thereof, and the chains may comprise one or a plurality of repeat units;

wherein the system is a pourable liquid above the dissolution temperature and the system is a stable gel below the gelling temperature;

wherein the system is pH stable in the range from pH=2 to pH=12; and wherein the system is water resistant and has superior adhesion properties.

* * * * *